United States Patent [19]

Nakamura et al.

[11] Patent Number: 4,977,179

[45] Date of Patent: Dec. 11, 1990

[54] PROLINE DERIVATIVES

[75] Inventors: Shizuo Nakamura, Naruto; Masatoshi Inai; Makoto Inoue, both of Tokushima; Kazushi Nagao, Naruto; Yoshiaki Tsuda, Anan, all of Japan

[73] Assignee: Otsuka Pharmaceutical Factory, Inc., Tokushima, Japan

[21] Appl. No.: 341,234

[22] Filed: Apr. 19, 1989

Related U.S. Application Data

[63] Continuation of Ser. No. 1,779, Jan. 9, 1987, abandoned.

[30] Foreign Application Priority Data

| | | | |
|---|---|---|---|
| Jan. 17, 1986 | [JP] | Japan | 61-8634 |
| Apr. 14, 1986 | [JP] | Japan | 61-85797 |
| Dec. 9, 1986 | [JP] | Japan | 61-293782 |

[51] Int. Cl.$^5$ .................... A61K 31/40; C07D 207/12
[52] U.S. Cl. ..................... 514/423; 548/533
[58] Field of Search ............ 514/423; 548/533

[56] References Cited

U.S. PATENT DOCUMENTS

| | | | |
|---|---|---|---|
| 4,374,829 | 2/1983 | Harris et al. | 424/177 |
| 4,472,380 | 9/1984 | Harris et al. | 424/177 |
| 4,506,082 | 3/1985 | Crossley | 548/533 |
| 4,512,979 | 4/1985 | Patchett et al. | 548/533 X |
| 4,525,301 | 6/1985 | Henning et al. | 548/533 X |
| 4,626,545 | 12/1986 | Taub | 548/533 X |
| 4,642,355 | 2/1987 | Nakamura et al. | 548/533 X |
| 4,661,515 | 4/1987 | Neiss et al. | 548/533 X |
| 4,886,813 | 12/1989 | Nakamura et al. | 514/423 X |

FOREIGN PATENT DOCUMENTS

| | | |
|---|---|---|
| 0012401 | 6/1980 | European Pat. Off. . |
| 0050800 | 5/1982 | European Pat. Off. . |
| 55-81845 | 6/1980 | Japan . |
| 2045771A | 11/1980 | United Kingdom . |

*Primary Examiner*—Joseph Paul Brust
*Attorney, Agent, or Firm*—Armstrong, Nikaido, Marmelstein, Kubovcik & Murray

[57] ABSTRACT

Disclosed is a proline derivative of the formula

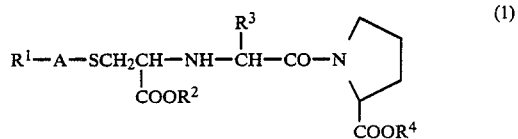

or a pharmaceutically acceptable salt thereof. These derivatives have useful utilities such as activity of inhibiting angiotensin converting enzyme.

14 Claims, No Drawings

PROLINE DERIVATIVES

This application is a continuation of application Ser. No. 001,779 filed Jan. 9, 1987 and now abandoned.

This invention relates to novel proline derivatives and salts thereof.

The proline derivatives of this invention are represented by the formula (1)

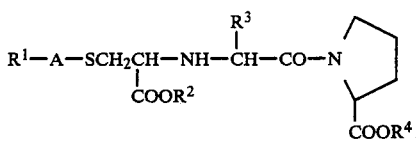

wherein:

$R^1$ is $C_1-C_8$ alkyl, $C_3-C_8$ cycloalkyl, $C_3-C_8$ cycloalkyl-$C_1-C_6$ alkyl, phenyl-$C_1-C_6$ alkyl, $C_2-C_6$ alkenyl, $C_2-C_6$ alkynyl, hydrogen, phenyl, benzoyl, trihalogeno-$C_1-C_6$ alkoxy-carbonyl, phenyl-$C_1-C_6$ alkoxy-carbonyl or $C_1-C_6$ alkoxycarbonyl, $R^2$ and $R^4$ are the same or different and each represent hydrogen or $C_1-C_6$ alkyl, $R^3$ is $C_1-C_6$ alkyl, and A represents $X-(Y)_n$ wherein X is sulfur, oxygen, NH group, NR' group (in which R' is $C_1-C_6$ alkyl, phenyl-$C_1-C_6$ alkyl or $C_3-C_8$ cycloalkyl) or a 5-or 6-membered saturated heterocyclic residue having nitrogen, Y is $C_1-C_6$ alkylene which may have phenyl, and n is 0 or 1 with the proviso that when X is the group other than sulfur, n is 1.

Given below are examples of groups represented by $R^1$, $R^2$, $R^3$, $R^4$, R', X and Y in the formula (1) and the corresponding respective groups in the other formulas to be described later.

Examples of $C_1-C_6$ alkyl groups are straight chain or branched chain lower alkyl groups having 1 to 6 carbon atoms such as methyl, ethyl, propyl, butyl, pentyl, hexyl, isopropyl, isobutyl, t-butyl, isoamyl, neopentyl, 4-methylpentyl and the like. Examples of $C_1-C_8$ alkyl groups are the alkyl groups exemplified above and straight chain or branched chain alkyl groups such as heptyl, octyl, 5-methylhexyl and the like.

Examples of $C_3-C_8$ cycloalkyl groups are cyclopropyl, cyclobutyl, cyclopentyl, cyclohexyl, cycloheptyl, cyclooctyl, etc.

Examples of $C_3-C_8$ cycloalkyl-$C_1-C_6$ alkyl groups are cyclopropylmethyl, cyclobutylmethyl, cyclopentylmethyl, cyclohexylmethyl, cyclooctylmethyl, 1-cyclopentylethyl, 2-cyclopentylethyl, 1-cyclohexylethyl, 2-cyclohexylethyl, 1-cyclohexylpropyl, 2-cyclohexylpropyl, 3-cyclohexylpropyl, 4-cyclohexylbutyl, etc.

Examples of phenyl-$C_1-C_6$ alkyl groups are benzyl, 1-phenylethyl, 2-phenylethyl, 3-phenylpropyl, 4-phenylbutyl, 5-phenylpentyl, 6-phenylhexyl, etc.

Examples of $C_2-C_6$ alkenyl groups are vinyl, allyl, 2-butenyl, 3-butenyl, 3-methyl-2-butenyl, 1-methylallyl, 2-pentenyl, 2-hexenyl, etc.

Examples of $C_2-C_6$ alkynyl groups are 1-ethynyl, 1-propynyl, 2-propynyl, 2-butynyl, 3-butynyl, 3-pentynyl, 4-pentynyl, 3-hexynyl, etc.

Examples of trihalogeno-$C_1-C_6$ alkoxy-carbonyl groups are trifluoromethoxycarbonyl, trichloromethoxycarbonyl, tribromomethoxycarbonyl, triiodomethoxycarbonyl, 2,2,2-trichloroethoxycarbonyl, 2,2,2-tribromoethoxycarbonyl, 3,3,3-trichloropropoxycarbonyl, 1-methyl-2,2,2-trichloroethoxycarbonyl, 1,1-dimethyl-2,2,2-trichloroethoxycarbonyl, 4,4,4-tribromobutoxycarbonyl, 5,5,5-trifluoropentyloxycarbonyl, 6,6,6-trichlorohexyloxycarbonyl, etc.

Examples of phenyl-$C_1-C_6$ alkoxy-carbonyl groups are benzyloxycarbonyl, 1-phenylethoxycarbonyl, 2-phenylethoxycarbonyl, 3-phenylpropoxycarbonyl, 4-phenylbutoxycarbonyl, 2-phenyl-2-methylpropoxycarbonyl, 5-phenylpentyloxycarbonyl, 6-phenylhexyloxycarbonyl, etc.

Examples of $C_1-C_6$ alkoxy-carbonyl groups are methoxycarbonyl, ethoxycarbonyl, propoxycarbonyl, isopropoxycarbonyl, butoxycarbonyl, t-butoxycarbonyl, pentyloxycarbonyl, hexyloxycarbonyl, etc.

Examples of heterocyclic rings forming 5- or 6-membered saturated heterocyclic residue having nitrogen include pyrrolidine rings and piperidine rings.

Examples of $C_1-C_6$ alkylene groups which may have phenyl are methylene, ethylene, trimethylene, tetramethylene, 2-methyl-1-trimethylene, 2,2-dimethylethylene, pentamethylene, isopropylethylene, isobutylethylene, hexamethylene, phenylmethylene, phenylethylene, benzylethylene, 2-phenyltrimethylene, 2-phenyltetramethylene, 3-phenylpentamethylene, 3-phenylhexamethylene, etc.

A class of proline derivatives of the formula (1) according to this invention are compounds represented by the formula

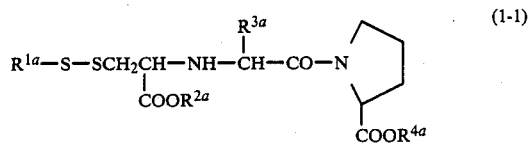

wherein $R^{1a}$ is $C_1-C_8$ alkyl or phenyl, $R^{2a}$ is $C_1-C_6$ alkyl, $R^{3a}$ is $C_1-C_6$ alkyl and $R^{4a}$ is hydrogen or $C_1-C_6$ alkyl.

Another class of proline derivatives of the invention are compounds represented by the formula

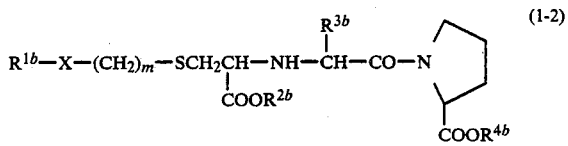

wherein $R^{1b}$ is $C_1-C_8$ alkyl, $C_3-C_8$ cycloalkyl, $C_3-C_8$ cycloalkyl-$C_1-C_6$ alkyl, phenyl, phenyl-$C_1-C_6$ alkyl, $C_2-C_6$ alkenyl or $C_2-C_6$ alkynyl, $R^{2b}$ and $R^{4b}$ are the same or different and each represent hydrogen or $C_1-C_6$ alkyl, $R^{3b}$ is $C_1-C_6$ alkyl, and X is sulfur or oxygen and m is a integer of 1 to 5.

A further class of proline derivatives of the invention are compounds represented by the formula

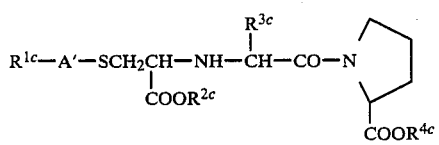  (1-3)

wherein $R^{1c}$ is hydrogen, benzoyl, trihalogeno-$C_1$-$C_6$ alkoxy-carbonyl, phenyl-$C_1$-$C_6$ alkoxy-carbonyl or $C_1$-$C_6$ alkoxy-carbonyl, $R^{2c}$ and $R^{4c}$ are the same or different and each represent hydrogen or $C_1$-$C_6$ alkyl, $R^{3c}$ is $C_1$-$C_6$ alkyl, and A' represents X-(Y)$_n$ in which X is oxygen, NH group, NR' group (wherein R' is $C_1$-$C_6$ alkyl, phenyl-$C_1$-$C_6$ alkyl or $C_3$-$C_8$ cycloalkyl) or a 5- or 6-membered saturated heterocyclic residue having nitrogen, Y is $C_1$-$C_6$ alkylene which may have phenyl, and n is 1.

Of the proline derivatives of the formula (1), preferred compounds are those wherein $R^1$ is $C_1$-$C_8$ alkyl or $C_3$-$C_8$ cycloalkyl, $R^2$ and $R^4$ are the same or different and each represent hydrogen or $C_1$-$C_6$ alkyl, $R^3$ is $C_1$-$C_6$ alkyl and A represents X-(Y)$_n$ in which X is sulfur or oxygen, Y is $C_1$-$C_6$ alkylene and n is 1 and most preferred compounds are those wherein $R^1$ is $C_4$-$C_6$ cycloalkyl, $R^2$ and $R^4$ are the same or different and each represent hydrogen or $C_1$-$C_6$ alkyl, $R^3$ is methyl and A represents X-(Y)$_n$ in which X is sulfur or oxygen, Y is $C_1$-$C_6$ alkylene and n is 1.

Examples of the preferred proline derivatives of the invention are as follows:

N-[(R)-1-ethoxycarbonyl-2-(2-butylthioethylthio)ethyl]-alanyl-(S)-proline methyl ester ($\beta$-isomer),
N-[(R)-1-ethoxycarbonyl-2-(2-butoxyethylthio)ethyl]-alanyl-(S)-proline methyl ester ($\beta$-isomer),
N-[(R)-1-ethoxycarbonyl-2-(2-cyclohexylthioethylthio)ethyl]-alanyl-(S)-proline methyl ester ($\beta$-isomer),
N-[(R)-1-carboxyl-2-(2-butoxyethylthio)ethyl]-alanyl-(S)-proline ($\beta$-isomer),
N-[(R)-1-ethoxycarbonyl-2-(2-cyclopentylthioethylthio)ethyl]-alanyl-(S)-proline methyl ester ($\beta$-isomer),
N-[(R)-1-ethoxycarbonyl-2-(2-cyclopentyloxyethylthio)ethyl]-alanyl-(S)-proline methyl ester ($\beta$-isomer),
N-[(R)-1-ethoxycarbonyl-2-(2-butoxyethylthio)ethyl]-alanyl-(S)-proline ($\beta$-isomer),
N-[(R)-1-ethoxycarbonyl-2-(2-butylthioethylthio)ethyl]-alanyl-(S)-proline ($\beta$-isomer),
N-[(R)-1-ethoxycarbonyl-2-(2-cyclohexylthioethylthio)ethyl]-alanyl-(S)-proline ($\beta$-isomer),
N-[(R)-1-ethoxycarbonyl-2-(2-cyclopentylthioethylthio)ethyl]-alanyl-(S)-proline ($\beta$-isomer), and
N-[(R)-1-ethoxycarbonyl-2-pentyldithioethyl]-alanyl-(S)-proline methyl ester ($\beta$-isomer).

The compounds of the formula (1) have asymmetric carbon atoms in the molecule and therefore optical isomers exist. The present invention includes all the isomers of the compounds.

The salts of the proline derivatives of the formula (1) according to the invention include pharmaceutically acceptable acid addition salts. Examples of acidic compounds useful for forming the acid addition salts are inorganic acids such as hydrochloric acid, sulfuric acid, nitric acid, phosphoric acid, hydrobromic acid and the like, and organic acids such as maleic acid, fumaric acid, malic acid, tartaric acid, citric acid, benzoic acid, benzenesulfonic acid, methanesulfonic acid and the like.

Of the proline derivatives of the formula (1) according to the invention, those having one or more acidic groups can be converted into salts by being acted on by a pharmaceutically acceptable base. The invention includes such salts. Examples of bases useful for forming such salts in the invention are inorganic bases such as sodium hydroxide, potassium hydroxide, calcium hydroxide, sodium carbonate, potassium hydrogencarbonate and the like and organic bases such as lysine, arginine, ornithine, morpholine, piperazine, piperidine, ethylamine, dimethylamine, triethylamine, dicyclohexylamine and the like.

The proline derivatives of the invention and salts thereof have an angiotensin converting enzyme-inhibitory activity and are useful for diagnosing, preventing and treating hypertension. The derivatives of the invention exhibit long-lasting effects, and are unlikely to cause kidney disorders and of low toxicity. Further the derivatives of the invention and salts thereof have an immunity-enhancing effect, expectorant activity, activity of reducing the intraocular pressure and activity of reducing lipid level, and therefore can be used as an immunostimulant, expectorant, agent for treating glaucoma, or agent for treating hyperlipemia.

The proline derivatives of the formula (1) according to the invention can be prepared by various processes, for example, those as described below in Reaction Schemes 1 to 5.

<Reaction Scheme 1>

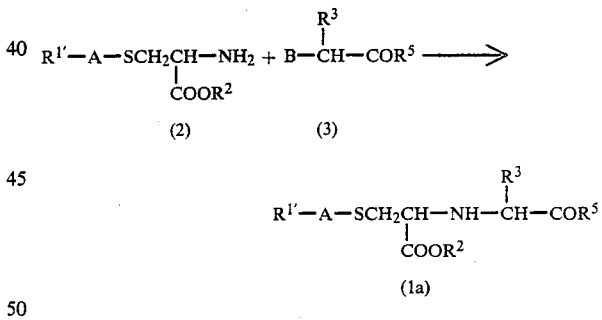

In the foregoing formulas, $R^2$, $R^3$ and A are as defined above, $R^{1'}$ represents $R^1$ group other than hydrogen, $R^5$ is hydroxyl, $C_1$-$C_6$ alkoxy, diphenyl, methyloxy, p-methoxybenzyloxy or a group

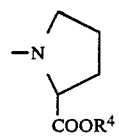

(wherein $R^4$ is as defined above), and B is halogen, alkylsulfonyloxy or arylsulfonyloxy.

Representative of halogen atoms represented by B in the compound (3) are chlorine, bromine, iodine and the like. Illustrative of alkylsulfonyloxy groups in the compound (3) are methanesulfonyloxy, trifluoromethanesulfonyloxy, ethanesulfonyloxy and the like. Typical of arylsulfonyloxy groups in the compound (3) are p-toluenesulfonyloxy, benzenesulfonyloxy, p-chlorobenezenesulfonyloxy and the like.

According to the process shown in Reaction Scheme 1, the cysteine derivative (2) is reacted with the compound (3) to give the compound (1a). The reaction is conducted in a suitable solvent in the presence of an acid binder. Examples of useful solvents are alcohols such as methanol, ethanol, 2-propanol, t-butanol and the like; ethers such as diethyl ether, tetrahydrofuran (THF), dioxane and the like; and aprotic polar solvents such as N,N-dimethylformamide (DMF), dimethylsulfoxide (DMSO), hexamethylphosphoric triamide (HMPA) and the like. Examples of useful acid binders are alkali metal carbonates such as sodium carbonate, potassium carbonate and the like, and alkali metal hydrogencarbonates such as sodium hydrogencarbonate, potassium hydrogencarbonate and the like; organic tertiary amines such as triethylamine, 1,8-diazabicyclo[5,4,0]-undecane-7-ene (DBU) and the like, and aromatic amines such as pyridine and the like. The acid binder is used in an amount of about 1 to about 2 moles, preferably about 1 to about 1.2 moles, per mole of the cysteine derivative (2). The compound (3) is usually used in an amount of at least about 1 mole, preferably about 1 to about 1.2 moles, per mole of the cysteine derivative (2). The reaction is conducted usually at 0° to about 80° C., preferably at or around room temperature and is completed in about 3 to about 72 hours.

The cysteine derivative (2) which is used as one of the starting materials in the reaction can be synthesized in accordance with the processes disclosed, for example, in Chemistry Letters, 981(1979), J. Org. Chem., 16, 749 (1959), Helv. Chim. Acta., 32, 866 (1949), J. Biol. Chem., 140, 131 (1941), Arch. Pharm. (Weinheim) 316, 934 (1983), J. Amer. Chem. Soc., 74, 828 (1952), etc.

<Reaction Scheme 2>

$$R^{1'}-A-SCH_2CH-NH-CH-COR^{5'} \longrightarrow$$
$$\phantom{R^{1'}-A-SCH_2CH-NH-}|\phantom{CH-COR^{5'}}$$
$$\phantom{R^{1'}-A-SCH_2CH-NH-}COOR^2$$

(1a')

$$R^{1'}-A-SCH_2CH-NH-CH-COR^{5''}$$
$$\phantom{R^{1'}-A-SCH_2CH-NH-}|$$
$$\phantom{R^{1'}-A-SCH_2CH-NH-}COOR^2$$

(1a'')

In the foregoing formulas, $R^{1'}$, $R^2$, $R^3$ and A are as defined in the formula (1), $R^{5'}$ is t-butoxy, p-methoxybenzyloxy, diphenylmethyloxy or a group

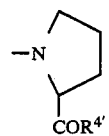

($R^{4'}$ is t-butoxy, p-methoxybenzyloxy, or diphenylmethyloxy), and $R^{5''}$ is hydroxyl or a group

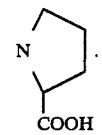

According to the process shown in Reaction Scheme 2, the compound (1a'') can be prepared without producing any by-product by treating the compound (1a') with an acid in the absence or in the presence of a scavenger, such as anisole, thioanisole, dimethylsulfide and the like.

Examples of acids useful in the acid treatment are trifluoroacetic acid (TFA), methanesulfonic acid, trifluoromethanesulfonic acid, hydrogen chloride, hydrogen bromide, hydrogen fluoride, acetic acid and the like. Of these examples, TFA, hydrogen chloride, acetic acid and the like are preferred. The reaction can be performed in the absence or in the presence of a solvent which does not adversely affect the reaction. Suitable examples of the solvents are ethers such as diethyl ether, THF, dioxane and the like; esters such as methyl acetate, ethyl acetate and the like; and halogenated hydrocarbons such as methylene chloride, chloroform and the like. The scavenger such as anisole and the like is used in an amount of usually about 1 to 10 moles, preferably about 3 to about 5 moles, per mole of the compound (1a'). The reaction is conducted at 0° to about 50° C., preferably 0° to about 25° C. and is completed in about 1 hour to about 10 hours.

<Reaction Scheme 3>

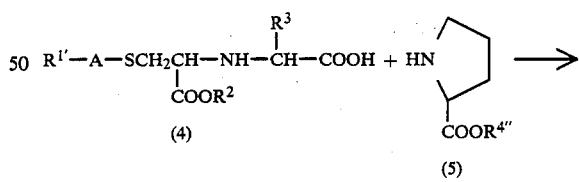

(4)

(5)

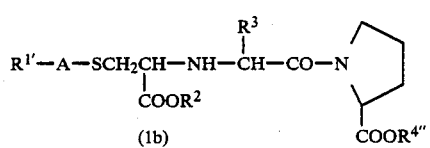

(1b)

In the foregoing formulas, $R^{1'}$, $R^2$, $R^3$ and A are as defined in the formula (1), and $R^{4''}$ is $C_1$-$C_6$ alkyl.

According to Reaction Scheme 3, the compound (1b) of this invention can be produced by treating the carboxylic acid (4) obtained in Reaction Schemes 1 and 2 with the amine (5). The reaction can be conducted by various processes according to amide bond-forming reaction, for example, as stated below.

(a) A condensation reaction in which the carboxylic acid (4) is condensed with the amine (5) in the presence of a condensing agent.

(b) A mixed anhydride method in which the carboxylic acid (4) is treated with an alkyl haloformate to obtain a mixed anhydride with which the amine (5) is allowed to react.

(c) An activated ester method in which the carboxylic acid (4) is made into an active ester such as p-nitrophenyl ester, N-hydroxysuccinimide ester, N-hydroxy-5-norbornene-2,3-dicarboximide ester or the like which is then treated with the amine (5).

(d) A carboxylic acid halide method in which the halide of the carboxylic acid (4) is treated with the amine (5).

(e) Other processes

For example, the carboxylic acid (4) is treated with a dehydrating agent such as acetic anhydride to obtain an acid anhydride with which the amine (5) is allowed to react. It is also possible as another option to treat the amine (5), at a high temperature and under a high pressure, with an ester of the carboxylic acid (4) and lower alcohol.

The processes described above in (a) to (e) can be carried out under substantially the same conditions as those for conventional respective processes. Of the foregoing processes, the process (a) is preferred and hereinafter described in detail. The process (a) employs a condensing agent such as N,N'-dicyclohexylcarbodiimide (DCC), DCC-N-hydroxysuccinimide, DCC-N-hydroxybenzotriazole, DCC-N-hydroxy-5-norbornene-2,3-dicarboximide, diphenylphosphorylazide (DPPA)-triethylamine, diethylphosphorocyanidate (DEPC)-triethylamine, etc. The reaction is conducted generally in a suitable solvent. Useful solvents can be any of various conventional solvents which do not adversely affect the reaction. Examples of suitable solvents are halogenated hydrocarbons such as methylene chloride, chloroform, dichloroethane and the like; aromatic hydrocarbons such as benzene, toluene, xylene and the like; ethers such as diethyl ether, THF, dioxane and the like; esters such as methyl acetate, ethyl acetate and the like; and aprotic polar solvents such as DMF, DMSO, HMPA and the like. The amount of the amine (5) used is usually at least about 1 mole, preferably about 1 to about 1.2 moles, per mole of the carboxylic acid (4). The condensing agent is used in an amount of about 1 to about 2 moles, preferably about 1 to about 1.2 moles, per mole of the carboxylic acid (4). The reaction is conducted at generally about $-20°$ to about 30° C., preferably about $-10°$ C. to room temperature, and is completed in about 3 to about 24 hours.

<Reaction Scheme-4>

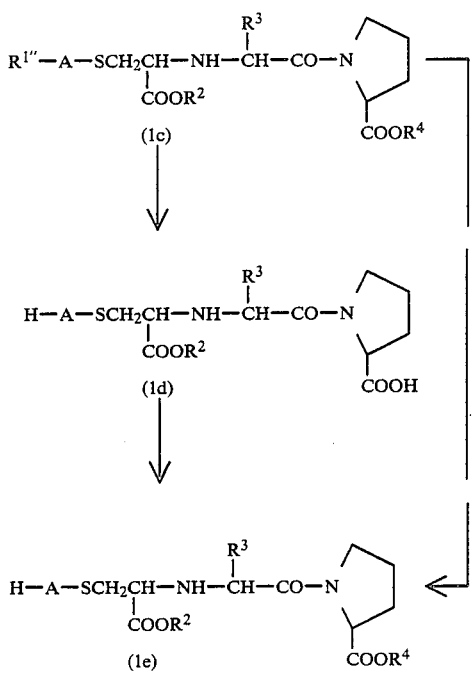

In the formulas $R^{1''}$ is trihalogeno-$C_1$–$C_6$ alkoxy-carbonyl (which includes 2,2,2-trichloroethoxycarbonyl, 2,2,2-tribromoethoxycarbonyl, 2,2,2-triiodoethoxycarbonyl and 1,1-dimethyl-2,2,2-trichloroethoxycarbonyl), phenyl-$C_1$–$C_6$ alkoxy-carbonyl (which includes benzyloxycarbonyl) or $C_1$–$C_6$ alkoxy-carbonyl (which includes t-butoxycarbonyl), and $R^2$, $R^3$, $R^4$ and A are as defined above.

According to the processes shown in Reaction Scheme 4, the compound (1c) is treated with an acid in the absence or the presence of anisole, thioanisole, dimethylsulfide or like scavenger, or is subjected to reduction using metal or metal salt, whereby the compounds (1d) and/or (1e) can be prepared without producing any byproduct. From the compound (1c) wherein $R^4$ is t-butyl can be selectively produced the compound (1d), and from the compound (1c) wherein $R^4$ is other alkyl can be selectively produced the compound (1e).

Examples of acids useful in the acid treatment are trifluoroacetic acid (TFA), methanesulfonic acid, trifluoromethanesulfonic acid, hydrogen chloride, hydrogen bromide, hydrogen fluoride, acetic acid and the like. The reaction can be performed in the absence or presence of a solvent, e.g. ethers such as diethyl ether, THF, dioxane and the like; esters such as methyl acetate, ethyl acetate and the like; and halogenated hydrocarbons such as methylene chloride, chloroform and the like. The scavenger such as anisole and the like is used in an amount of usually about 1 to 10 moles, preferably about 3 to about 5 moles, per mole of the compound (1c). The reaction is conducted at 0° to about 50° C., preferably 0° to about 25° C. and is completed in about 1 hour to about 10 hours.

The reduction using metal or metal salt is conducted in a conventional manner. For example, the reaction is performed using zinc, tin, stannous chloride, preferably zinc, in a suitable solvent. Examples of suitable solvents are acetic acid, formic acid, hydrochloric acid and like acidic solvents, diethyl ether, THF, dioxane and like ethers, DMF and like aprotic polar solvents, acetonitrile, mixtures thereof, etc. The metal or metal salt is used in an amount of about 3 to about 30 moles, preferably about 7 to about 20 moles, per mole of the compound (1c). The reaction is carried out at a temperature of 0° to about 70° C., preferably at or around room temperature and is completed in about 2 to about 15 hours.

<Reaction Scheme 5>

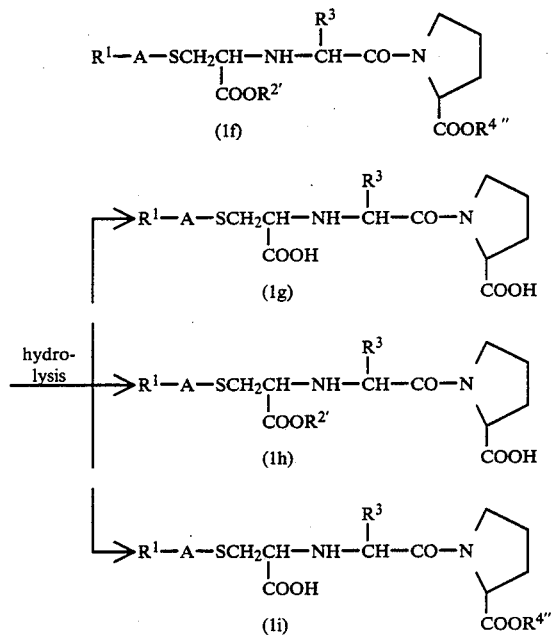

In the foregoing formulas, $R^1$, $R^3$, $R^{4''}$ and A are as defined above, and $R^2$, is $C_1-C_6$ alkyl.

According to the processes as shown in Reaction Scheme 5, the compound (1f) of the invention is hydrolyzed in the presence of a basic compound to give the compound (1g), (1h) or (1i) of the invention.

The hydrolysis is conducted in water or in a mixture of water and a suitable organic solvent. Examples of suitable organic solvents are lower alcohols such as methanol, ethanol and the like; ethers such as diethyl ether, THF, dioxane and the like; acetonitrile; etc. Examples of useful basic compounds are alkali metal hydroxides such as sodium hydroxide, potassium hydroxide, lithium hydroxide, etc. In the hydrolysis, the proportions of the products formed vary depending on the reaction temperature, reaction time and amount of the basic compound used, especially on the amount of the basic compound used. Specifically, if the amount of the basic compound used is about 2.2 to about 3.5 moles per mole of the compound (1f), the compound (1g) will be formed selectively. On the other hand, if the amount of the basic compound used is about 1 to about 3 moles per mole of the compound (1f), the compounds (1g), (1h) and (1i) are produced as a mixture. The hydrolysis reactions are usually conducted at a temperature of 0° to about 40° C., preferably at room temperature, and are completed in about 0.5 to about 12 hours.

The compounds obtained in the reactions shown above in Reaction Schemes can be easily separated from the reaction mixture and purified by conventional separation methods including solvent extraction, dilution, distillation and recrystallization methods, column chromatography, preparative thin-layer chromatography, ion-exchange chromatography, etc.

For use as pharmaceuticals, the compound of this invention can be administered to humans as it is or as formulated into pharmaceutical compositions in combination with conventional pharmaceutically acceptable carriers. The dosage form of pharmaceutical compositions is not specifically limited but can be suitably determined according to a specific purpose. For oral compositions, tablets, powders, granules, solutions and the like are available. Parenteral preparations include injectable solutions and the like. The daily dose of the active component in the pharmaceutical composition is not specifically limited but can be suitably determined over a wide range. Generally it ranges from about 0.06 to about 50 mg/kg body weight/day, preferably about 0.06 to about 10 mg/kg body weight/day, in order to achieve the contemplated result. About 1 to about 500 mg of the active component is used per dosage unit.

Pharmaceutical preparations having incorporated therein the compound of the present invention as an active component can be prepared by conventional methods. For the preparation of tablets, the compound of the invention is mixed with a pharmaceutically acceptable excipient such as gelatin, starch, lactose, magnesium stearate, talc, gum arabic and the like. For the preparation of capsules, the compound of the invention is mixed with a pharmaceutically acceptable inert filler or diluent and the mixture is dividedly placed in hard gelatin or soft gelatin capsules or the like. Syrups or elixirs can be prepared by mixing the compound of the invention with sweetening such as saccharose, antiseptic such as methyl- or propyl-paraben, coloring agent, flavoring or the like. For the production of parenteral preparations, the compound of the invention is dissolved in a sterilized liquid carrier. Preferred carriers are water and physiological saline. Liquid preparations having the desired transparency, stability and suitability for parenteral administration can be prepared by dissolving about 1 to about 500 mg of active component in water and an organic solvent and also in polyethylene glycol having a molecular weight of about 200 to about 5000. Preferred liquid preparations are those containing a lubricant such as sodium carboxymethyl cellulose, methyl cellulose, polyvinyl pyrrolidone, polyvinyl alcohol, etc. The liquid preparations may further have incorporated therein a bactericide and fungicide such as benzyl alcohol, phenol, thimerosal and the like, and when required, saccharose, sodium chloride or like isotonic agent, stabilizer, buffer, etc. To improve the stability, parenteral preparations filled into containers are lyophilized for removal of water by methods known in the art. The lyophilized powder can be reconstituted before use.

This invention will be described below in greater detail with reference to the following examples for preparation of the compounds of the invention and reference examples for preparation of starting materials useful for production of the compounds of the invention.

The terms "α-isomer" and "β-isomer" are used to mean the following.

Of the two isomers produced as the reaction products of S-substituted-L-cysteine ethyl ester and 2-bromopropionic acid t-butyl ester, a first eluate obtained in silica gel column chromatography (using ether/n-hexane) is hereinafter referred to as "α-isomer" and a second eluate therefrom as "β-isomer". Also the compounds derived from the α-isomer are called "α-isomers" and those from the β-isomer are called "β-isomers".

REFERENCE EXAMPLE 1

Preparation of N-[(R)-1-ethoxycarbonyl-2-heptyldithioethyl]-alanine t-butyl ester (α- and β-isomers)

A 14.8 g quantity of S-heptylthio-L-cysteine ethyl ester and 11.1 g of 2-bromopropionic acid t-butyl ester were dissolved in 20 ml of HMPA. To the solution was added 7.4 ml of triethylamine and the mixture was stirred at room temperature for 60 hours. The reaction mixture was poured into ice water and the mixture was extracted with ethyl acetate. The extract was washed with water and with a saturated sodium chloride solution and dried over anhydrous sodium sulfate. The solvent was evaporated off under reduced pressure and the residue was separated and purified by silica gel column chromatography (a 1:3 mixture of ether and n-hexane as an eluent), producing the α-isomer of the title compound as a colorless oil from the first eluate. Yield 2.14 g.

$[\alpha]_D^{18} + 33.3°$ (c=1.4, ethanol).

NMR (CDCl$_3$): δ 0.89 (3H, t, J=6 Hz), 1.27 (3H, d, J=7 Hz), 1.29 (3H, t, J=7 Hz), 1.45 (9H, s), 1.5–1.9 (10H, m), 2.71 (2H, t, J=7 Hz), 2.98 (2H, d, J=6.5 Hz), 3.32 (1H, q, J=7 Hz), 3.57 (1H, t, J=6.5 Hz), 4.20 (2H, q, J=7 Hz).

The β-isomer of the title compound was obtained as a colorless oil from the second eluate. Yield 2.69 g. $[\alpha]_D^{18} = -19.8°$ (c=0.9, ethanol). NMR (CDCl$_3$): δ 0.89 (3H, t, J=6 Hz), 1.29 (3H, d, J=7 Hz), 1.30 (3H, t, J=7 Hz), 1.47 (9H, s), 1.5–1.8 (10H, m), 2.1 (1H, brs), 2.72 (2H, t, J=7 Hz), 2.88 (1H, dd, J=7 Hz, 13 Hz), 3.06 (1H, dd, J=6 Hz, 13 Hz), 3.30 (1H, q, J=7 Hz), 3.64 (1H, dd, J=6 Hz, 7 Hz), 4.21 (2H, q, J=7 Hz).

REFERENCE EXAMPLES 2 TO 7

The compounds as listed below in Table 1 were obtained by following the general procedure of Reference Example 1.

TABLE 1

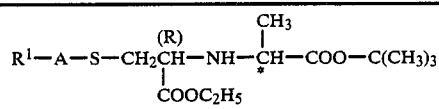

$$R^1-A-S-CH_2\overset{(R)}{CH}-NH-\overset{*}{\underset{COOC_2H_5}{CH}}-\overset{\overset{CH_3}{|}}{\underset{}{}}COO-C(CH_3)_3$$

| Ref. Ex. No. | R$^1$ | A | Isomer (*) | Optical Rotation (Ethanol) | NMR(CDCl$_3$): δ |
|---|---|---|---|---|---|
| 2 | CH$_3$(CH$_2$)$_2$— | S | α | $[\alpha]_D^{18} = +40.7°$ (c = 0.9) | 0.99 (3H, t, J=7Hz), 1.28 (3H, d, J=7Hz), 1.45 (9H, s), 1.71 (2H, sextet, J=7Hz), 2.69 (2H, t, J=7Hz), 2.99 (2H, d, J=6Hz), 3.33 (1H, q, J=7Hz), 3.58 (1H, q, J=7Hz), 4.20 (2H, q, J=7Hz), |
| 3 | CH$_3$(CH$_2$)$_2$— | S | β | $[\alpha]_D^{18} = -30.4°$ (c = 0.9) | 0.99 (3H, t, J=7Hz), 1.29 (3H, d, J=7Hz), 1.30 (3H, t, J=7Hz), 1.47 (9H, s), 1.70 (2H, sextet, J=7Hz), 2.0 (1H, br s), 2.70 (2H, t, J=7Hz) 2.87 (1H, dd, J=8Hz, 13Hz), 3.06 (1H, dd, J=6Hz, 13Hz), 3.30 (1H, q, J=7Hz), 3.64 (1H, dd, J=6Hz, 8Hz), 4.21 (2H, q, J=7Hz) |
| 4 | CH$_3$(CH$_2$)$_4$— | S | α | $[\alpha]_D^{17} = +33.9°$ (c = 0.9) | 0.90 (3H, t, J=5.5Hz), 1.27 (3H, d, J=7Hz), 1.29 (3H, t, J=7Hz), 1.45 (9H, s), 1.5–1.9 (6H, m), 2.71 (2H, t, J=7Hz), 2.97 (2H, d, J=6.5Hz), 3.32 (1H, q, J=7Hz), 3.58 (1H, t, J=6.5Hz), 4.20 (2H, q, J=7Hz) |
| 5 | CH$_3$(CH$_2$)$_4$— | S | β | $[\alpha]_D^{17} = -25.8°$ (c = 1.1) | 0.90 (3H, t, J=5.5Hz), 1.28 (3H, d, J=7Hz), 1.30 (3H, t, J=7Hz), 1.47 (9H, s), 1.5–1.9 (6H, m), 2.1 (1H, br s), |

TABLE 1-continued $$R^1-A-S-CH_2\underset{COOC_2H_5}{\underset{|}{C}H}-NH-\underset{*}{\overset{CH_3}{\underset{|}{C}H}}-COO-C(CH_3)_3$$

| Ref. Ex. No. | $R^1$ | A | Isomer (*) | Optical Rotation (Ethanol) | NMR(CDCl$_3$): δ |
|---|---|---|---|---|---|
| | | | | | 2.71 (2H, t, J=7Hz) |
| | | | | | 2.86 (1H, dd, J=7Hz, 13Hz), |
| | | | | | 3.05 (1H, dd, J=6Hz, 13Hz), |
| | | | | | 3.56 (1H, q, J=7Hz), |
| | | | | | 3.64 (1H, dd, J=6Hz, 7Hz), |
| | | | | | 4.21 (2H, q, J=7Hz) |
| 6 | phenyl | S | α | $[α]_D^{17} = +73.5°$ (c = 0.9) | 1.24 (3H, t, J=7Hz), |
| | | | | | 1.26 (3H, t, J=7Hz), |
| | | | | | 1.44, 1.46 (total 9H, each s), |
| | | | | | 2.4 (1H, br s), |
| | | | | | 2.94 (1H, dd, J=7Hz, 13Hz), |
| | | | | | 3.11 (1H, dd, J=6Hz, 13Hz), |
| | | | | | 3.26 (2H, q, J=7Hz), |
| | | | | | 3.58 (1H, dd, J=6Hz, 7Hz), |
| | | | | | 4.17 (2H, q, J=7Hz) |
| | | | | | 7.2 -7.6 (5H, m) |
| 7 | phenyl | S | β | $[α]_D^{17} = -19.2°$ (c = 1.0) | 1.26 (3H, d, J=7Hz), |
| | | | | | 1.27 (3H, t, J=7Hz), |
| | | | | | 1.47 (9H, s), 2.1 (1H, br s) |
| | | | | | 2.91 (1H, dd, J=7Hz, 13Hz) |
| | | | | | 3.10 (1H, dd, J=6Hz, 13Hz), |
| | | | | | 3.28 (1H, q, J=7Hz) |
| | | | | | 3.66 (1H, dd, J=6Hz, 7Hz), |
| | | | | | 4.18 (2H, q, J=7Hz) |
| | | | | | 7.2–7.6 (5H, m) |

REFERENCE EXAMPLE 8

Preparation of
N-[(R)-1-ethoxycarbonyl-2-heptyldithioethyl]-alanine
(β-isomer) hydrochloride A 2.6 g portion of β-isomer of N-[(R)-1-ethoxycarbonyl-2-heptyldithioethyl]-alanine t-butyl ester obtained in Reference Example 1 was dissolved in 30 ml of 4N-hydrochloride-dioxane. The solution was stirred at room temperature for 6 hours. The solvent was evaporated off under reduced pressure. To the residue was added ether to precipitate crystals which were collected by filtration. The crystals were recrystallized from dichloromethane-n-hexane, giving the hydrochloride of the title compound as a colorless powder. Yield 1.8 g. M.p. 105°–108° C.

$[α]_D^{21} = +50.5°$ (c=0.8, DMF).

REFERENCE EXAMPLE 9

Preparation of
N-[(R)-1-ethoxycarbonyl-2-propyldithioethyl]-alanine
(β-isomer) hydrochloride The compound was obtained by following the general procedure of Reference Example 8.
M.p. 118°–122° C.
$[α]_D^{21} = +58.3°$ (c=0.7, ethanol).

REFERENCE EXAMPLE 10

Preparation of
N-[(R)-1-ethoxycarbonyl-2-pentyldithioethyl]-alanine
(β-isomer)

In 4 ml of 25% HBr-acetic acid was dissolved 2.12 g of the β-isomer of N-[(R)-1-ethoxycarbonyl-2-pentyldithioethyl]-alanine t-butyl ester prepared in Reference Example 5. The solution was stirred at room temperature for 2 hours. The HBr-acetic acid was evaporated off under reduced pressure. The residue was poured into ice water and the mixture was adjusted to a pH of 4 with a saturated aqueous solution of sodium hydrogencarbonate. Then the mixture was extracted with dichloromethane. The extract was washed with water and dried over anhydrous sodium sulfate. The solvent was evaporated off under reduced pressure. To the residue was added n-hexane to precipitate crystals which were collected by filtration as the title compound in colorless powder form. Yield 0.89 g. M.p. 128°–131° C.

$[α]_D^{21} = -4.4°$ (c=0.7, DMF).

REFERENCE EXAMPLE 11

Preparation of
N-[(R)-1-ethoxycarbonyl-2-phenyldithioethyl]-alanine
(β-isomer)

The compound was obtained by following the general procedure of Reference Example 10.
M.p. 136°–138° C.
$[α]_D^{16} = +5.2°$ (c=0.5, DMF)

REFERENCE EXAMPLE 12

Preparation of
N-[(R)-1-ethoxycarbonyl-2-(2-propylthioethylthio)ethyl]-alanine t-butyl ester (α- and β-isomers)

In 50 ml of HMPA were dissolved 12.2 g of S-2-propylthioethyl-L-cysteine ethyl ester and 11.2 g of 2-bromopropionic acid t-butyl ester. A 7.5 ml quantity of triethylamine was added to the solution and the mixture was stirred at room temperature for 40 hours. The reaction mixture was poured into ice water and the mixture was extracted with ethyl acetate. The extract was washed with water and with a saturated sodium chloride solution and dried over anhydrous sodium sulfate. The solvent was evaporated off under reduced pressure and the residue was purified by silica gel column chromatography (a 1:3 mixture of ether and n-hexane as an eluent), giving the α-isomer of the title compound as a colorless oil from the first eluate. Yield 2.58 g.

$[\alpha]_D^{26} = +26.5°$ (c=0.7, ethanol).

NMR (CDCl$_3$): δ 0.99 (3H, t, J=7 Hz), 1.27 (3H, d, J=7 Hz), 1.29 (3H, t, J=7 Hz), 1.45 (9H, s), 2.84 (2H, d, J=6 Hz), 3.31 (1H, q, J=7 Hz), 3.41 (1H, t, J=6 Hz), 4.20 (2H, q, J=7 Hz)

The β-isomer of the title compound was obtained as a colorless oil from the second eluate. Yield 5.44 g.

$[\alpha]_D^{26} = -0°$ (c=0.8, ethanol). NMR (CDCl$_3$): δ 0.99 (3H, t, J=7 Hz), 1.29 (3H, d, J=7 Hz), 1.29 (3H, t, J=7 Hz), 1.46 (9H, s), 2.24 (1H, brs), 3.30 (1H, q, J=7 Hz), 4.20 (2H, q, J=7 Hz).

REFERENCE EXAMPLES 13 TO 36

The compounds as listed below in Table 2 were obtained by following the general procedure of Reference Example 12.

TABLE 2

$$R^1-X-(Y)_n-S-CH_2\overset{(R)}{CH}-NH-\overset{*}{\underset{COOC_2H_5}{\overset{CH_3}{CH}}}-COO-C(CH_3)_3$$

| Ref. Ex. No. | R$^1$ | —X—(Y)$_n$— | Isomer (*) | Optical Rotation | NMR(CDCl$_3$): δ |
|---|---|---|---|---|---|
| 13 | CH$_3$(CH$_2$)$_2$— | —S(CH$_2$)$_3$— | α | $[\alpha]_D^{23}$ = +26.8° (c = 1.4, ethanol) | 0.98 (3H, t, J=7Hz), 1.27 (3H, d, J=7Hz), 1.29 (3H, t, J=7Hz), 1.45 (9H, s), 4.20 (2H, q, J=7Hz) |
| 14 | CH$_3$(CH$_2$)$_2$— | —S(CH$_2$)$_3$— | β | $[\alpha]_D^{23}$ = −34.0° (c = 0.9, ethanol) | 0.99 (3H, t, J=7Hz), 1.29 (3H, d, J=7Hz), 1.29 (3H, t, J=7Hz), 1.46 (9H, s), 4.21 (2H, q, J=7Hz) |
| 15 | CH$_3$(CH$_2$)$_3$— | —S(CH$_2$)$_2$— | α | $[\alpha]_D^{18}$ = +25.0° (c = 1.0, ethanol) | 0.92 (3H, t, J=6.5Hz), 1.27 (3H, d, J=7Hz), 1.29 (3H, t, J=7Hz), 1.45 (9H, s), 2.84 (2H, d, J=6Hz), 3.31 (1H, q, J=7Hz), 3.61 (1H, t, J=6Hz), 4.20 (2H, q, J=7Hz) |
| 16 | CH$_3$(CH$_2$)$_3$— | —S(CH$_2$)$_2$— | β | $[\alpha]_D^{18}$ = −19.0° (c = 0.6, ethanol) | 0.99 (3H, t, J=6.5Hz), 1.29 (3H, d, J=7Hz), 1.29 (3H, t, J=7Hz), 1.46 (9H, s), 2.26 (1H, br s), 3.30 (1H, q, J=7Hz), 4.21 (2H, q, J=7Hz) |
| 17 | CH$_3$(CH$_2$)$_3$— | —O(CH$_2$)$_2$— | α | $[\alpha]_D^{23}$ = +23.0° (c = 0.6, methanol) | 0.99 (3H, t, J=7Hz), 1.27 (3H, d, J=7Hz), 1.29 (3H, t, J=7Hz), 1.45 (9H, s), 2.74 (2H, t, J=7Hz), 2.86 (2H, d, J=7Hz), 4.20 (2H, q, J=7Hz) |
| 18 | CH$_3$(CH$_2$)$_3$— | —O(CH$_2$)$_2$— | β | $[\alpha]_D^{23}$ = −38.5° (c = 0.8, methanol) | 0.91 (3H, t, J=7Hz), 1.29 (3H, t, J=7Hz), 1.29 (3H, d, J=7Hz), 1.47 (9H, s), 2.73 (2H, t, J=6.5Hz), 4.20 (2H, q, J=7Hz) |
| 19 | CH$_3$(CH$_2$)$_5$— | —S(CH$_2$)$_2$— | α | $[\alpha]_D^{24}$ = +23.5° (c = 0.9, ethanol) | 0.89 (3H, t, J=5.5Hz), 1.27 (3H, d, J=7Hz), 1.29 (3H, t, J=7Hz), 1.45 (9H, s), 2.84 (2H, d, J=6Hz), 3.46 (1H, t, J=6Hz), 4.20 (2H, q, J=7Hz) |
| 20 | CH$_3$(CH$_2$)$_5$— | —S(CH$_2$)$_2$— | β | $[\alpha]_D^{24}$ = −26.4° (c = 0.6, ethanol) | 0.91 (3H, t, J=5.5Hz), 1.29 (3H, d, J=7Hz), 1.29 (3H, t, J=7Hz), 1.46 (9H, s), 3.45 (1H, t, J=6Hz), 4.21 (2H, q, J=7Hz) |

TABLE 2-continued $$R^1-X-(Y)_n-S-CH_2\overset{(R)}{\underset{COOC_2H_5}{CH}}-NH-\overset{CH_3}{\underset{*}{CH}}-COO-C(CH_3)_3$$

| Ref. Ex. No. | R¹ | —X—(Y)ₙ— | Isomer (*) | Optical Rotation | NMR(CDCl₃): δ |
|---|---|---|---|---|---|
| 21 | CH₃<br>  \<br>   CH—CH₂—<br>  /<br>CH₃ | —S(CH₂)₂— | α | $[\alpha]_D^{25} = +27.0°$<br>(c = 0.9, methanol) | 0.99 (6H, d, J=6.5Hz),<br>1.28 (3H, d, J=7Hz),<br>1.29 (3H, t, J=7Hz),<br>1.45 (9H, s),<br>2.43 (2H, d, J=7Hz),<br>2.74 (4H, br s),<br>2.85 (2H, d, J=6Hz),<br>3.31 (1H, q, J=7Hz),<br>3.45 (1H, t, J=6Hz),<br>4.20 (2H, q, J=7Hz) |
| 22 | CH₃<br>  \<br>   CH—CH₂—<br>  /<br>CH₃ | —S(CH₂)₂— | β | $[\alpha]_D^{25} = -25.6°$<br>(c = 0.9, methanol) | 0.98 (6H, d, J=6.5Hz),<br>1.29 (3H, d, J=7Hz),<br>1.29 (3H, t, J=7Hz),<br>1.46 (9H, s),<br>2.24 (1H, br s),<br>2.43 (2H, d, J=6.5Hz),<br>2.73 (4H, s)<br>3.30 (1H, q, J=7Hz),<br>4.21 (2H, q, J=7Hz) |
| 23 | 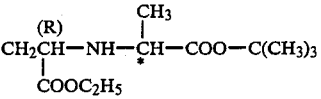 | —S(CH₂)₂— | α | $[\alpha]_D^{24} = +23.4°$<br>(c = 1.1, ethanol) | 1.27 (3H, d, J=7Hz),<br>1.29 (3H, t, J=7Hz),<br>1.45 (9H, s),<br>2.74 (4H, br s),<br>2.84 (2H, d, J=6Hz),<br>4.20 (2H, q, J=7Hz) |
| 24 | 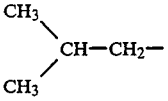 | —S(CH₂)₂— | β | $[\alpha]_D^{24} = -27.8°$<br>(c = 1.0, ethanol) | 1.29 (3H, d, J=7Hz),<br>1.30 (3H, t, J=7Hz),<br>1.47 (9H, s),<br>2.74 (4H, br s),<br>4.21 (2H, q, J=7Hz) |
| 25 | 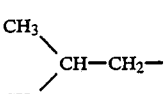—CH₂— | —S(CH₂)₂— | α | $[\alpha]_D^{25} = +6.3°$<br>(c = 1.0, ethanol) | 1.27 (3H, d, J=7Hz),<br>1.29 (3H, t, J=7Hz),<br>1.45 (9H, s),<br>2.42 (2H, d, J=6.5Hz)<br>2.72 (4H, br s)<br>2.84 (2H, d, J=6Hz)<br>4.20 (2H, q, J=7Hz) |
| 26 | —CH₂— | —S(CH₂)₂— | β | $[\alpha]_D^{25} = -12.6°$<br>(c = 1.0, ethanol) | 1.29 (3H, d, J=7Hz),<br>1.30 (3H, t, J=7Hz),<br>1.47 (9H, s),<br>2.43 (2H, d, J=7Hz)<br>2.72 (4H, br s)<br>4.21 (2H, q, J=7Hz) |
| 27 |  | —S(CH₂)₂— | α | $[\alpha]_D^{24} = +26.6°$<br>(c = 1.7 ethanol) | 1.23 (3H, d, J=7Hz),<br>1.27 (3H, t, J=7Hz),<br>1.44 (9H, s),<br>2.46 (1H, br s),<br>4.18 (2H, q, J=7Hz),<br>7.2–7.5 (5H, m) |
| 28 | 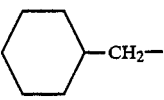 | —S(CH₂)₂— | β | $[\alpha]_D^{24} = -22.7°$<br>(c = 0.8, ethanol) | 1.28 (3H, d, J=7Hz),<br>1.28 (3H, t, J=7Hz),<br>1.45 (9H, s),<br>4.19 (2H, q, J=7Hz),<br>7.2–7.4 (5H, m) |
| 29 | 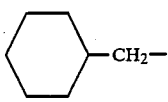—CH₂— | —S(CH₂)₂— | α | $[\alpha]_D^{22} = +27.4°$<br>(c = 0.8, methanol) | 1.26 (3H, d, J=7Hz),<br>1.28 (3H, t, J=7Hz),<br>1.45 (9H, s),<br>2.77 (2H, d, J=6Hz),<br>2.6–2.7 (4H, m),<br>3.73 (2H, s)<br>4.19 (2H, q, J=7Hz),<br>7.29 (5H, s) |

TABLE 2-continued $$R^1-X-(Y)_n-S-CH_2\underset{\underset{COOC_2H_5}{|}}{\overset{(R)}{CH}}-NH-\underset{*}{\overset{\overset{CH_3}{|}}{CH}}-COO-C(CH_3)_3$$

| Ref. Ex. No. | R¹ | —X—(Y)ₙ— | Isomer (*) | Optical Rotation | NMR(CDCl₃): δ |
|---|---|---|---|---|---|
| 30 | (benzyl) C₆H₅—CH₂— | —S(CH₂)₂— | β | $[\alpha]_D^{22} = -28.9°$ (c = 0.8, methanol) | 1.28 (3H, t, J=7Hz), 1.29 (3H, d, J=7Hz), 1.46 (9H, s), 2.5–2.8 (4H, m), 3.74 (2H, s), 4.20 (2H, q, J=7Hz), 7.29 (5H, s) |
| 31 | H₂C=CH—CH₂— | —S(CH₂)₂— | α | $[\alpha]_D^{24} = +25.1°$ (c = 1.1, ethanol) | 1.27 (3H, d, J=7Hz), 1.29 (3H, t, J=7Hz), 1.45 (9H, s), 2.46 (1H, br s), 2.83 (2H, d, J=6Hz), 3.16 (2H, d, J=7Hz), 3.46 (1H, t, J=6Hz), 4.20 (2H, q, J=7Hz), 4.9–5.3 (2H, m), 5.5–6.1 (1H, m) |
| 32 | H₂C=CH—CH₂— | —S(CH₂)₂— | β | $[\alpha]_D^{24} = -35.7°$ (c = 0.8, ethanol) | 1.30 (3H, d, J=7Hz), 1.30 (3H, t, J=7Hz), 1.47 (9H, s), 2.25 (1H, br s), 3.17 (2H, d, J=7Hz), 4.21 (2H, q, J=7Hz), 4.9–5.3 (2H, m), 5.5–6.1 (5H, m) |
| 33 | (CH₃)₂C=CH—CH₂— | —S(CH₂)₂— | α | $[\alpha]_D^{23} = +23.0°$ (c = 1.1, ethanol) | 1.28 (3H, d, J=7Hz), 1.29 (3H, t, J=7Hz), 1.45 (9H, s), 1.71 (6H, d, J=6Hz), 2.3 (1H, br s), 2.84 (2H, d, J=5.5Hz), 3.31 (1H, q, J=7Hz), 3.46 (1H, t, J=7Hz), 4.20 (2H, q, J=7Hz), 5.1–5.3 (1H, m) |
| 34 | (CH₃)₂C=CH—CH₂— | —S(CH₂)₂— | β | $[\alpha]_D^{23} = -28.5°$ (c = 1.0, ethanol) | 1.30 (3H, d, J=7Hz), 1.30 (3H, t, J=7Hz), 1.46 (9H, s), 1.71 (6H, d, J=7Hz), 2.2 (1H, br s), 2.71 (4H, br s), 3.37 (1H, q, J=7Hz), 3.47 (1H, dd, J=5.5Hz, 7.5Hz), 4.21 (2H, q, J=7Hz), 5.1–5.3 (1H, m) |
| 35 | H—C≡C—CH₂— | —S(CH₂)₂— | α | $[\alpha]_D^{23} = +25.0°$ (c = 0.6, ethanol) | 1.27 (3H, d, J=7Hz), 1.29 (3H, t, J=7Hz), 1.45 (9H, s), 2.27 (1H, t, J=2.5Hz), 2.6–3.1 (6H, m), 3.29 (2H, d, J=2.5Hz), 4.20 (2H, q, J=7Hz) |
| 36 | H—C≡C—CH₂— | —S(CH₂)₂— | β | $[\alpha]_D^{23} = -38.5°$ (c = 0.7, ethanol) | 1.30 (3H, d, J=7Hz), 1.30 (3H, t, J=7Hz), 1.47 (9H, s), 2.28 (1H, t, J=2.5Hz), 2.6–3.1 (6H, m), 3.30 (2H, d, J=2.5Hz), 4.21 (2H, q, J=7Hz) |

REFERENCE EXAMPLE 37

Preparation of N-[(R)-1-ethoxycarbonyl-2-(2-propylthioethylthio)ethyl]-alanine (β-isomer)

In 15 ml of 25% HBr-acetic acid was dissolved 5.3 g of β-isomer of N-[(R)-1-ethoxycarbonyl-2-(2-propylthioethylthio)ethyl]-alanine t-butyl ester prepared in Reference Example 12. The solution was stirred at room temperature for 1 hour. The excess of the solvent was evaporated off. The residue was poured into ice water and the mixture was adjusted to a pH of 4 with a saturated aqueous solution of sodium hydrogencarbonate. Then the mixture was extracted with dichloromethane.

The extract was washed with water and dried over anhydrous sodium sulfate. The solvent was evaporated off under reduced pressure. To the crystalline residue was added isopropyl ether to precipitate crystals which were collected by filtration and recrystallized from ethyl acetate-n-hexane. Thus the β-isomer of the title compound was obtained. Yield 1.91 g. M.p. 101°-102° C.

$[\alpha]_D^{26} = -19.6°$ (c=0.7, DMF).

REFERENCE EXAMPLES 38 TO 51

The compounds as listed below in Table 3 were obtained by following the general procedure of Reference Example 37.

TABLE 3

$$R^1-X-(Y)_n-S-CH_2\underset{COOC_2H_5}{\overset{(R)}{CH}}-NH-\underset{*}{\overset{CH_3}{CH}}-COOH$$

| Ref. Ex. No. | $R^1$ | $-X-(Y)_n-$ | Isomer (*) | Optical Rotation | M.p. (°C.) |
|---|---|---|---|---|---|
| 38 | $CH_3(CH_2)_2-$ | $-S-(CH_2)_3-$ | β | $[\alpha]_D^{28} = -19.8°$ (c = 0.6, DMF) | 110-111 |
| 39 | $CH_3(CH_2)_3-$ | $-S-(CH_2)_2-$ | β | $[\alpha]_D^{24} = -21.2°$ (c = 2.0, DMF) | 98-101 |
| 40 | $CH_3(CH_2)_3-$ | $-O-(CH_2)_2-$ | α | $[\alpha]_D^{22} = +16.5°$ (c = 0.6, DMF) | 115-117 |
| 41 | $CH_3(CH_2)_3-$ | $-O-(CH_2)_2-$ | β | $[\alpha]_D^{22} = -25.9°$ (c = 0.5, DMF) | 101-104 |
| 42 | $CH_3(CH_2)_5-$ | $-S-(CH_2)_2-$ | β | $[\alpha]_D^{25} = -2.8°$ (c = 0.8, methanol) | 97 |
| 43 | $(CH_3)_2CH-CH_2-$ | $-S-(CH_2)_2-$ | β | $[\alpha]_D^{28} = -19.3°$ (c = 1.2, DMF) | 109-112 |
| 44 | cyclohexyl- | $-S-(CH_2)_2-$ | β | $[\alpha]_D^{25} = -17.9°$ (c = 0.8, DMF) | 121-123 |
| 45 | cyclohexyl-$CH_2-$ | $-S-(CH_2)_2-$ | β | $[\alpha]_D^{26} = -17.6°$ (c = 0.8, DMF) | 109-116 |
| 46 | phenyl- | $-S-(CH_2)_2-$ | β | $[\alpha]_D^{26} = -14.4°$ (c = 0.6, DMF) | 130-131 |
| 47 | phenyl-$CH_2-$ | $-S-(CH_2)_2-$ | α | $[\alpha]_D^{22} = +18.9°$ (c = 0.6, DMF) | 120-122 |
| 48 | phenyl-$CH_2-$ | $-S-(CH_2)_2-$ | β | $[\alpha]_D^{22} = -19.8°$ (c = 0.7, DMF) | 97-100 |
| 49 (hydrochloride) | $CH_2=CH-CH_2-$ | $-S-(CH_2)_2-$ | α | $[\alpha]_D^{28} = +28.5°$ (c = 0.7, DMF) | 113-115 |
| 50 | $(CH_3)_2C=CH-CH_2-$ | $-S-(CH_2)_2-$ | β | $[\alpha]_D^{24} = -16.7°$ (c = 1.2, DMF) | 78-88 |
| 51 | $H-C\equiv C-CH_2-$ | $-S-(CH_2)_2-$ | β | $[\alpha]_D^{22} = -22.6°$ (c = 0.5, DMF) | 97-100 |

REFERENCE EXAMPLE 52

Preparation of N-[(R)-1-ethoxycarbonyl-2-[(S)-2-benzyloxycarbonylamino-3-phenylpropylthio]ethyl]-alanine t-butyl ester (α-isomer)

A 46 g quantity of S-[(S)-2-benzyloxycarbonylamino-3-phenylpropyl]-L-cysteine ethyl ester and 27 g of 2-bromopropionic acid t-butyl ester were dissolved in 150 ml of HMPA. To the solution was added 18 ml of triethylamine and the mixture was stirred at room temperature for 48 hours. The reaction mixture was poured into ice water and the mixture was extracted with ethyl acetate. The extract was washed with water and with a saturated sodium chloride solution and dried over anhydrous sodium sulfate. The solvent was evaporated off under reduced pressure and the residue was separated and purified by silica gel column chromatography (a 5:4 mixture of ether and n-hexane as an eluent), giving the α-isomer of the title compound as a colorless oil from the first eluate. Yield 10.6 g.

$[\alpha]_D^{22} = +22.6°$ (c=1.1, ethanol).

NMR (CDCl$_3$): δ 1.26 (3H, t, J=7 Hz), 1.44 (9H, s), 2.69 (2H, d, J=5.5 Hz), 4.18 (2H, q, J=7 Hz), 5.07 (2H, s), 7.23 (5H, s), 7.32 (5H, s).

REFERENCE EXAMPLES 53 TO 72

The compounds as listed below in Table 4 were obtained by following the general procedure of Reference Example 52.

In Table 4, Z stands for benzyloxycarbonyl group, Boc for t-butoxycarbonyl group, and Troc for 2,2,2-trichloroethoxycarbonyl group (these abbreviations are also used in the subsequent tables).

TABLE 4

$$R^1-X-(Y)_n-S-CH_2\overset{(R)}{\underset{COOC_2H_5}{CH}}-NH-\overset{CH_3}{\underset{*}{CH}}-COO-C(CH_3)_3$$

| Ref. Ex. No. | R$^1$ | —X—(Y)$_n$— | Isomer (*) | Optical Rotation (ethanol) | NMR(CDCl$_3$): δ |
|---|---|---|---|---|---|
| 53 | Z | —NH—CH(CH$_2$—C$_6$H$_5$)—CH$_2$— (S) | β | $[\alpha]_D^{22} = -14.7°$ (c = 1.1) | 1.26 (3H, t, J=7Hz), 1.27 (3H, d, J=7Hz), 1.43 (9H, s), 3.29 (1H, q, J=7Hz), 4.17 (2H, q, J=7Hz), 5.06 (2H, s), 7.26 (5H, s), 7.31 (5H, s) |
| 54 | Z | —NH—CH(CH$_2$—C$_6$H$_5$)—CH$_2$— (R) | α | $[\alpha]_D^{22} = +10.9°$ (c = 1.3) | 1.21 (3H, d, J=7Hz), 1.26 (3H, t, J=7Hz), 1.44 (9H, s), 2.69 (2H, d, J=5.5Hz), 3.27 (1H, q, J=5.5Hz), 3.42 (1H, t, J=7Hz), 4.17 (2H, q, J=7Hz), 5.08 (2H, s), 7.22 (5H, s), 7.32 (5H, s) |
| 55 | Z | —NH—CH(CH$_2$—C$_6$H$_5$)—CH$_2$— (R) | β | $[\alpha]_D^{22} = -33.4°$ (c = 1.0) | 1.26 (3H, t, J=7Hz), 1.26 (3H, d, J=7Hz), 1.44 (9H, s), 2.5–3.1 (6H, m), 4.18 (2H, q, J=7Hz), 5.08 (2H, s), 7.23 (5H, s), 7.31 (5H, s) |
| 56 | Boc | —NH—CH(CH$_2$—C$_6$H$_5$)—CH$_2$— (R) | β | $[\alpha]_D^{23} = -34.3°$ (c = 1.0) | 1.28 (3H, t, J=7Hz), 1.30 (3H, d, J=7Hz), 1.41 (9H, s), 1.46 (9H, s), 2.6–3.0 (6H, m), 4.19 (2H, q, J=7Hz), 7.24 (5H, s) |
| 57 | Troc | —N(piperidine)—(CH$_2$)$_2$— | α | $[\alpha]_D^{22} = +12.6°$ (c = 0.8) | 1.27 (3H, d, J=7Hz), 1.29 (3H, t, J=7Hz), 1.45 (9H, s), 4.20 (2H, q, J=7Hz), 4.74 (2H, s) |
| 58 | Troc | —N(piperidine)—(CH$_2$)$_2$— | β | $[\alpha]_D^{22} = -22.8°$ (c = 1.2) | 1.30 (3H, t, J=7Hz), 1.30 (3H, d, J=7Hz), 1.46 (9H, s), 4.21 (2H, q, J=7Hz), 4.74 (2H, s) |

TABLE 4-continued $$R^1-X-(Y)_n-S-CH_2\overset{(R)}{\underset{COOC_2H_5}{CH}}-NH-\overset{CH_3}{\underset{*}{CH}}-COO-C(CH_3)_3$$

| Ref. Ex. No. | R[1] | —X—(Y)ₙ— | Isomer (*) | Optical Rotation (ethanol) | NMR(CDCl₃): δ |
|---|---|---|---|---|---|
| 59 | Boc | —NH—CH(CH₂—C₆H₅)—CH₂— (S) | β | [α]_D^23 = −15.9° (c = 1.1) | 1.28 (3H, t, J=7Hz), 1.30 (3H, d, J=7Hz), 1.41 (9H, s), 1.46 (9H, s), 2.68 (2H, d, J=6Hz), 3.31 (1H, q, J=7Hz), 4.19 (2H, q, J=7Hz), 7.24 (5H, s) |
| 60 | Z | —NH—CH(C₆H₅)—CH₂— (R) | β | [α]_D^22 = +6.2° (c = 0.7) | 1.24 (3H, t, J=7Hz), 1.24 (3H, d, J=7Hz), 2.70 (2H, d, J=6Hz), 2.99 (2H, d, J=6Hz), 4.15 (2H, q, J=7Hz), 5.08 (2H, s), 7.29 (5H, s) |
| 61 | Z | —NH—(CH₂)₂— | β | [α]_D^25 = −27.0° (c = 0.8) | 1.28 (3H, t, J=7Hz), 1.28 (3H, d, J=7Hz), 1.44 (9H, s), 4.19 (2H, q, J=7Hz), 5.10 (2H, s), 7.33 (5H, s) |
| 62 | Boc | —NH—(CH₂)₂— | β | [α]_D^23 = −28.7° (c = 1.1) | 1.29 (3H, t, J=7Hz), 1.30 (3H, d, J=7Hz), 1.44 (9H, s), 1.46 (9H, s), 4.21 (2H, q, J=7Hz) |
| 63 | Boc | —NH—(CH₂)₃— | β | [α]_D^20 = −24.3° (c = 0.6) | 1.29 (3H, t, J=7Hz), 1.30 (3H, d, J=7Hz), 1.44 (9H, s), 1.47 (9H, s), 2.60 (2H, t, J=7Hz), 4.21 (2H, q, J=7Hz) |
| 64 | Boc | —NH—(CH₂)₆— | β | [α]_D^23 = −19.5° (c = 0.9) | 1.29 (3H, t, J=7Hz), 1.29 (3H, d, J=7Hz), 1.44 (9H, s), 1.47 (9H, s), 2.54 (2H, t, J=7Hz), 4.21 (2H, q, J=7Hz), |
| 65 | Troc | —N((CH₂)₂CH₃)—(CH₂)₂— | β | [α]_D^22 = −24.4° (c = 0.6) | 0.91 (3H, t, J=7Hz), 1.30 (3H, t, J=7Hz), 1.30 (3H, d, J=7Hz), 1.46 (9H, s), 2.6-3.0 (4H, m), 3.2-3.7 (6H, m), 4.21 (2H, q, J=7Hz), 4.76 (2H, s) |
| 66 | Z | —NH—CH(CH(CH₃)₂)—CH₂— (S) | β | [α]_D^21 = +2.0° (c = 1.2) | 0.90 (3H, d, J=6.5Hz), 0.93 (3H, d, J=6.5Hz), 1.27 (3H, t, J=7Hz), 1.27 (3H, d, J=7Hz), 1.44 (9H, s), 2.6-3.1 (4H, m), 3.28 (1H, q, J=7Hz), 4.19 (2H, q, J=7Hz), 5.10 (2H, s), 7.33 (5H, s) |
| 67 | Z | —NH—CH(CH(CH₃)(CH₂CH₃))—CH₂— (S)(S) | α | [α]_D^23 = +40.2° (c = 0.7) | 0.8-1.0 (6H, m), 1.28 (3H, t, J=7Hz), 1.44 (9H, s), 2.75 (2H, d, J=6.5Hz), 2.82 (2H, d, J=6.5Hz), 4.19 (2H, q, J=7Hz), 5.11 (2H, s) 7.34 (5H, s) |
| 68 | Z | —NH—CH(CH(CH₃)(CH₂CH₃))—CH₂— (S)(S) | β | [α]_D^23 = +0.3° (c = 0.7) | 0.8-1.0 (6H, m), 1.24 (3H, t, J=7Hz), 1.28 (3H, d, J=7Hz), 1.44 (9H, s), 2.6-2.9 (4H, m), 4.19 (2H, q, J=7Hz), 5.10 (2H, s), 7.34 (5H, s), |

TABLE 4-continued $$R^1-X-(Y)_n-S-CH_2\overset{(R)}{C}H-NH-\overset{CH_3}{\underset{*}{C}H}-COO-C(CH_3)_3$$
$$\underset{COOC_2H_5}{|}$$

| Ref. Ex. No. | R¹ | —X—(Y)ₙ— | Isomer (*) | Optical Rotation (ethanol) | NMR(CDCl₃): δ |
|---|---|---|---|---|---|
| 69 | Boc | H₃C   CH₂CH₃<br>  \\ /<br>  (S) CH<br>—NH—CH—CH₂—<br>       (S) | β | $[\alpha]_D^{23} = -3.2°$<br>(c = 0.5) | 0.8–1.0 (6H, m),<br>1.29 (3H, d, J=7Hz),<br>1.29 (3H, t, J=7Hz),<br>1.44 (9H, s),<br>1.46 (9H, s),<br>2.72 (2H, d, J=5.5Hz),<br>4.20 (2H, q, J=7Hz), |
| 70 | Troc | —N(S)⟨pyrrolidine⟩—CH₂— | β | $[\alpha]_D^{22} = -50.4°$<br>(c = 0.7) | 1.28 (3H, d, J=7Hz),<br>1.29 (3H, t, J=7Hz),<br>1.46 (9H, s),<br>1.8–2.2 (4H, m),<br>2.5–3.2 (4H, m),<br>3.3–3.7 (4H, m),<br>4.20 (2H, q, J=7Hz)<br>4.73 (2H, s) |
| 71 | Troc | CH₂—C₆H₅<br>\|<br>—N—(CH₂)₂— | β | $[\alpha]_D^{21} = -20.3°$<br>(c = 0.5) | 1.28 (3H, d, J=7Hz),<br>1.28 (3H, t, J=7Hz),<br>2.5–2.9 (4H, m),<br>3.1–3.6 (4H, m),<br>4.19 (2H, q, J=7Hz),<br>4.58 (2H, s),<br>4.82 (2H, s),<br>7.30 (5H, s) |
| 72 | Troc | —O—(CH₂)₂— | β | $[\alpha]_D^{22} = -24.6°$<br>(c = 0.8) | 1.29 (3H, t, J=7Hz),<br>1.29 (3H, d, J=7Hz),<br>1.46 (9H, s),<br>3.30 (1H, q, J=7Hz),<br>4.21 (2H, q, J=7Hz),<br>4.38 (2H, t, J=7Hz)<br>4.77 (2H, s) |

REFERENCE EXAMPLE 73

Preparation of
N-[(R)-1-ethoxycarbonyl-2-[(S)-2-benzyloxycarbonylamino-3-phenylpropylthio]ethyl]-alanine
(β-isomer)

In a mixture of 50 ml of TFA and 10 ml of anisole was dissolved 20.1 g of β-isomer of N-[(R)-1-ethoxycarbonyl-2-[(S)-2-benzyloxycarbonylamino-3-phenylpropylthio]ethyl]-alanine t-butyl ester prepared in Reference Example 53. The solution was stirred at room temperature for 5 hours. The excess of the solvent was evaporated off. The residue was poured into ice water and the mixture was adjusted to a pH of 4 with a saturated aqueous solution of sodium hydrogencarbonate. Then the mixture was extracted with dichloromethane. The extract was washed with water and dried over anhydrous sodium sulfate. The solvent was evaporated off under reduced pressure. To the crystalline residue was added ether to precipitate crystals which were collected by filtration and recrystallized from dichloromethane-ether. Thus the β-isomer of the title compound was obtained. Yield 8.63 g. M.p. 124°–127° C.

$[\alpha]_D^{22} = -2.2°$ (c=0.7, DMF).

REFERENCE EXAMPLES 74 TO 86

The compounds as listed below in Table 5 were obtained by following the general procedure of Reference Example 73.

The compound obtained in Reference Example 73 was also listed in Table 5.

TABLE 5

$$R^1-X-(Y)_n-S-CH_2\overset{(R)}{CH}-NH-\overset{CH_3}{\underset{*}{CH}}-COOH$$
$$\phantom{R^1-X-(Y)_n-S-CH_2}COOC_2H_5$$

| Ref. Ex. No. | $R^1$ | —X—(Y)$_n$— | Isomer (*) | Optical Rotation | M.p. (°C.) |
|---|---|---|---|---|---|
| 73 | Z | —NH—CH(CH₂-phenyl)—CH₂— (S) | β | $[\alpha]_D^{22} = -2.2°$ (c=0.7, DMF) | 124–127 |
| 74 (hydrochloride) | Z | —NH—CH(CH₂-phenyl)—CH₂— (S) | α | $[\alpha]_D^{22} = +27.5°$ (c=0.8, DMF) | 155–159 |
| 75 (hydrochloride) | Z | —NH—CH(CH₂-phenyl)—CH₂— (R) | α | $[\alpha]_D^{22} = +17.2°$ (c=0.8, DMF) | 141–148 |
| 76 | Z | —NH—CH(CH₂-phenyl)—CH₂— (R) | β | $[\alpha]_D^{22} = -14.3°$ (c=0.7, DMF) | 142–143 |
| 77 | Z | —NH—(CH₂)₂— | β | $[\alpha]_D^{25} = -10.5°$ (c=0.5, ethanol) | 104–105 |
| 78 | Troc | —N(piperidyl)—(CH₂)₂— | β | $[\alpha]_D^{24} = -14.7°$ (c=0.7, DMF) | 145–149 |
| 79 | Z | —NH—CH(phenyl)—CH₂— (R) | β | $[\alpha]_D^{24} = -14.5°$ (c=0.6, DMF) | 107–110 |
| 80 | Troc | —N((CH₂)₂CH₃)—(CH₂)₂— | β | $[\alpha]_D^{24} = +16.8°$ (c=0.5, DMF) | 108–109 |
| 81 | Z | —NH—CH(CH(CH₃)₂)—CH₂— (S) | β | $[\alpha]_D^{21} = +26.5°$ (c=0.7, DMF) | 117–122 |
| 82 | Z | —NH—CH(CH(S)(CH₃)(CH₂CH₃))—CH₂— (S) | α | $[\alpha]_D^{24} = +55.3°$ (c=0.7, DMF) | 117–119 |
| 83 | Z | —NH—CH(CH(S)(CH₃)(CH₂CH₃))—CH₂— (S) | β | $[\alpha]_D^{24} = +30.0°$ (c=0.7, DMF) | 129–131 |

TABLE 5-continued $$R^1-X-(Y)_n-S-CH_2\overset{(R)}{\underset{COOC_2H_5}{CH}}-NH-\overset{CH_3}{\underset{*}{CH}}-COOH$$

| Ref. Ex. No. | R¹ | —X—(Y)$_n$— | Isomer (*) | Optical Rotation | M.p. (°C.) |
|---|---|---|---|---|---|
| 84 | Troc | —N(S)—CH(—)—CH$_2$—CH$_2$—CH$_2$— (pyrrolidine) | β | $[\alpha]_D^{22} = -45.4°$ (c=0.7, DMF) | 126–129 |
| 85 | Troc | —N(—(CH$_2$)$_2$—)—CH$_2$—C$_6$H$_5$ | β | $[\alpha]_D^{21} = -10.1°$ (c=0.7, DMF) | 136–139.5 |
| 86 | Troc | —O—(CH$_2$)$_2$— | β | $[\alpha]_D^{21} = -17.4°$ (c=0,6, DMF) | 121-124 |

REFERENCE EXAMPLE 87

Preparation of N-[(R)-1-ethoxycarbonyl-2-[(S)-2-t-butoxycarbonylamino-3-phenylpropylthio]ethyl]-alanine (β-isomer)

In 15 ml of 25% HBr-acetic acid was dissolved 4.6 g of β-isomer of N-[(R)-1-ethoxycarbonyl-2-[(S)-2-t-butoxycarbonylamino-3-phenylpropylthio]ethyl]-alanine t-butyl ester prepared in Reference Example 59. The solution was stirred at room temperature for 30 minutes. To the reaction mixture was added ether to precipitate crystals which were collected by filtration and were dissolved in 25 ml of DMF. A 2.8 ml quantity of triethylamine and 2.1 g of di-t-butyldicarbonate were added to the solution with ice cooling and stirring. The reaction mixture was further stirred at room temperature for 14 hours. Then the mixture was poured into ice water, adjusted to a pH of 4 with 10% aqueous solution of citric acid and extracted with ethyl acetate. The extract was washed with water and dried over anhydrous sodium sulfate. The solvent was evaporated off under reduced pressure. To the residue was added ether to precipitate crystals which were collected by filtration as the title compound. Yield 2.9 g. M.p. 112°–114° C.

$[\alpha]_D^{23} = -8.8°$ (c=0.6, ethanol).

REFERENCE EXAMPLES 88 TO 90

The compounds as listed below in Table 6 were obtained by following the general procedure of Reference Example 87.

TABLE 6

$$Boc-NH-(CH_2)_m-S-CH_2\overset{(R)}{\underset{COOC_2H_5}{CH}}-NH-\overset{CH_3}{\underset{*}{CH}}-COOH$$

| Ref. Ex. No. | m | Isomer (*) | Optical Rotation | M.p. (°C.) |
|---|---|---|---|---|
| 88 | 2 | β | $[\alpha]_D^{23} = -15.2°$ (c=0.7, DMF) | 128–130 |
| 89 | 3 | β | $[\alpha]_D^{18} = -12.9°$ (c=0.7, ethanol) | 117–120 |
| 90 | 6 | β | $[\alpha]_D^{21} = -13.9°$ (c=0.8, ethanol) | 102–106 |

REFERENCE EXAMPLE 91

Preparation of N-[(R)-1-ethoxycarbonyl-2-[(2S,3S)-2-benzoylamino-3-methylpentylthio]ethyl]-alanine (β-isomer)

In 25 ml of TFA was dissolved 6.7 g of β-isomer of N-[(R)-1-ethoxycarbonyl-2-[(2S,3S)-2-t-butoxycarbonylamino-3-methylpentylthio]ethyl]-alanine t-butyl ester prepared in Reference Example 69. The solution was stirred at room temperature for 3 hours. The excess of the solvent was evaporated off under reduced pressure. The residue was dissolved in DMF and the solution was neutralized by the addition of triethylamine with ice cooling. Further, 2 ml of triethylamine was added to the solution. A 3.5 g quantity of benzoic anhydride was added thereto. The mixture was stirred at room temperature over night. The reaction mixture was poured into ice water and adjusted to a pH of 8 to 9 with a saturated aqueous solution of sodium hydrogencarbonate, followed by washing with ether. The aqueous phase was adjusted to a pH of 4 with 1N hydrochloric acid and extracted with ethyl acetate. The extract was washed with water and dried over anhydrous sodium sulfate. The solvent was evaporated off under reduced pressure. To the residue was added ether to precipitate crystals which were collected by filtration as the title compound.

Yield 2.7 g. M.p. 133°–136° C.
$[\alpha]_D^{23} = +60.3°$ (c=0.5, DMF).

REFERENCE EXAMPLES 92 TO 96

The compounds as listed below in Table 7 were obtained by following the general procedure of Reference Example 1.

TABLE 7

$$R^1-X-(Y)_n-S-CH_2\underset{COOC_2H_5}{\overset{(R)}{CH}}-NH-\underset{*}{\overset{CH_3}{CH}}-COO-C(CH_3)_3$$

| Ref. Ex. No. | R¹ | —X—(Y)ₙ— | Isomer (*) | Optical Rotation (ethanol) | NMR (CDCl₃): δ |
|---|---|---|---|---|---|
| 92 |  | —S(CH₂)₂— | β | $[\alpha]_D^{21} = -17.3°$ (c=0.8) | 1.29 (3H, t, J=7Hz), 1.29 (3H, d, J=7Hz), 1.46 (9H, s), 2.76 (4H, br s), 4.21 (2H, q, J=7Hz) |
| 93 |  | —O(CH₂)₂— | β | $[\alpha]_D^{26} = -36.2°$ (c=1.1) | 1.30 (3H, t, J=7Hz), 1.36 (3H, d, J=7Hz), 1.47 (9H, s), 2.8–3.1 (2H, m), 3.3–3.5 (1H, m), 3.58 (2H, t, J=7Hz), 3.8–3.9 (1H, m), 4.22 (2H, q, J=7Hz) |
| 94 | Troc | 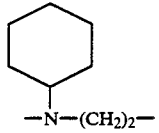 —N—(CH₂)₂— | α | $[\alpha]_D^{25} = +14.3°$ (c=0.7) | 1.28 (3H, d, J=7Hz), 1.29 (3H, t, J=7Hz), 1.45, 1.48 (total 9H, each s), 1.5–1.9 (10H, m), 2.6–3.0 (4H, m), 3.2–3.6 (4H, m), 3.7–4.0 (2H, m), 4.1–4.4 (2H, m), 4.76 (2H, s) |
| 95 | Troc | 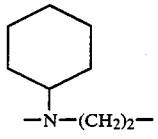 —N—(CH₂)₂— | β | $[\alpha]_D^{25} = -15.0°$ (c=0.9) | 1.30 (3H, t, J=7Hz), 1.30 (3H, d, J=7Hz), 1.45, 1.46 (totol 9H, each s), 1.5–1.9 (10H, m), 2.6–3.1 (4H, m), 3.2–3.6 (4H, m), 3.7–4.0 (2H, m), 4.21 (2H, q, J=7Hz), 4.77 (2H, s) |
| 96 |  | —S(CH₂)₃— | β | $[\alpha]_D^{23} = -25.0°$ (c=0.9) | 1.30 (3H, t, J=7Hz), 1.33 (3H, d, J=7Hz), 1.47 (9H, s), 2.80 (1H, dd, J=8Hz, 13Hz), 2.94 (1H, dd, J=5Hz, 13Hz), 3.08 (1H, quintet, J=7Hz), 3.36 (1H, q, J=7Hz), 3.50 (1H, dd, J=5Hz, 8Hz), 4.22 (2H, q, J=7Hz) |

REFERENCE EXAMPLES 97 TO 101

The compounds as listed below in Table 8 were obtained by following the general procedure of Reference Example 8.

TABLE 8

$$R^1-X-(Y)_n-S-CH_2\overset{(R)}{\underset{COOC_2H_5}{CH}}-NH-\overset{CH_3}{\underset{*}{CH}}-COOH$$

| Ref. Ex. No. | R¹ | —X—(Y)ₙ— | Isomer (*) | Optical Rotation | M.p. (°C.) |
|---|---|---|---|---|---|
| 97 | cyclopentyl | —S(CH₂)₂— | β | $[\alpha]_D^{21} = -1.7°$ (c=0.6, methanol) | 115–118 |
| 98 | cyclopentyl | —O(CH₂)₂— | β | $[\alpha]_D^{25} = -26.0°$ (c=0.8, DMF) | 109–112 |
| 99 (hydrochloride) | Troc | cyclohexyl-N—(CH₂)₂— | α | $[\alpha]_D^{25} = +14.5°$ (c=0.8, methanol) | 74–79 |
| 100 | Troc | cyclohexyl-N—(CH₂)₂— | β | $[\alpha]_D^{25} = -7.1°$ (c=0.7, methanol) | 115–118 |
| 101 | cyclopentyl | —S(CH₂)₃— | β | $[\alpha]_D^{23} = -18.5°$ (c=1.0, DMF) | 121–123 |

EXAMPLE 1

Preparation of N-[(R)-1-ethoxycarbonyl-2-heptyldithio-7 ethyl]-alanyl-(S)-proline methyl ester (β-isomer) and maleate thereof A 500 mg portion of hydrochloride of β-isomer of N-[(R)-1-ethoxycarbonyl-2-heptyldithioethyl]-alanine obtained in Reference Example 8 and 340 mg of hydrochloride of (S)-proline methyl ester were dissolved in 15 ml of DMF. To the solution was added with ice cooling and stirring a solution of 260 mg of DEPC (90% content) in 2 ml of DMF. A solution of 410 mg of triethylamine in 3 ml of DMF was added dropwise thereto. The mixture was stirred for 12 hours while being slowly returned to room temperature. To the reaction mixture were added water and a saturated aqueous solution of sodium hydrogencarbonate to obtain a weakly alkaline solution. The solution was extracted with ethyl acetate. The extract was washed with water and with a saturated sodium chloride solution and dried over anhydrous sodium sulfate. The solvent was evaporated off under reduced pressure, giving a crude product of the β-isomer of the title compound as a colorless oil. Yield 558 mg.

The β-isomer obtained above (558 mg) was dissolved in 15 ml of methanol. To the solution was added a solution of 140 mg of maleic acid in 10 ml of methanol. The solution was concentrated and n-hexane was added to the solution to precipitate the crystals. The crystals were recrystallized from ethyl acetate-n-hexane, collected by filtration and dried, giving the maleate of β-isomer of the title compound as a colorless powder.

Yield 413 mg.

$[\alpha]_D^{21} = -34.0°$ (c=0.9, ethanol).

M.p. 89°–93° C.

EXAMPLES 2 TO 4

The compounds as listed below in Table 9 were obtained by following the general procedure of Example 1.

TABLE 9

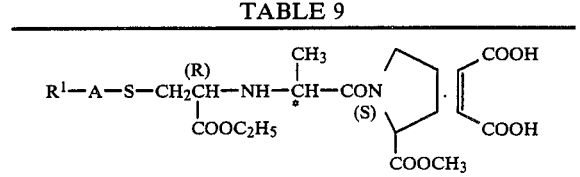

$$R^1-A-S-CH_2\overset{(R)}{\underset{COOC_2H_5}{CH}}-NH-\overset{CH_3}{\underset{*}{CH}}-CON\overset{(S)}{\phantom{X}}$$

| Example No. | A | R¹ | Isomer (*) | M.p. (°C.) (solvent) or NMR (CDCl₃): δ |
|---|---|---|---|---|
| 2 | S | CH₃(CH₂)₂— | β | 91–95° C. (ethyl acetate-n-hexane) |
| 3 | S | CH₃(CH₂)₄— | β | 99–101° C. (methanol-ether) |

TABLE 9-continued

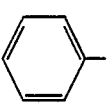

| Example No. | A | R¹ | Isomer (*) | M.p. (°C.) (solvent) or NMR (CDCl₃): δ |
|---|---|---|---|---|
| 4 | S | phenyl | β | 1.26 (3H, t, J=7Hz), 1.55 (3H, d, J=7Hz), 3.35 (3H s), 4.25 (2H, q, J=7hz), 6.29 (2H, s), 7.1–7.7 (5H, m) |

EXAMPLE 5

Preparation of N-[(R)-1-ethoxycarbonyl-2-heptyldithioethyl]-alanyl-(S)-proline t-butyl ester (β-isomer) and maleate thereof A 580 mg portion of the hydrochloride of β-isomer of N-[(R)-1-ethoxycarbonyl-2-heptyldithioethyl]-alanine obtained in Reference Example 8 and 282 mg of (S)-proline t-butyl ester were dissolved in 15 ml of DMF. To the solution was added with ice cooling and stirring a solution of 299 mg of DEPC (90% content) in 5 ml of DMF and further added dropwise a solution of 318 mg of triethylamine in 5 ml of DMF. The solution was stirred for 12 hours while being slowly returned to room temperature. Thereafter the reaction mixture was poured into ice water and the mixture was extracted with ethyl acetate. The organic phase was washed with 10% aqueous solution of citric acid, saturated aqueous solution of sodium hydrogencarbonate and a saturated aqueous solution of sodium chloride and dried over anhydrous sodium sulfate. The solvent was evaporated off under reduced pressure, giving a crude product of the β-isomer of the title compound as a colorless oil. Yield 650 mg.

The β-isomer obtained above (650 mg) was dissolved in 15 ml of ether. To the solution was added 150 mg of maleic acid and the solution was concentrated and n-hexane was added to the solution to precipitate the crystals. The crystals were collected by filtration and dried, giving the maleate of the title compound as a colorless powder. Yield 599 mg.

$[\alpha]_D^{21} = -28.0°$ (c=1.0, ethanol).

M.p. 81°–84° C.

EXAMPLE 6

Preparation of N-[(R)-1-ethoxycarbonyl-2-heptyldithioethyl]-alanyl-(S)-proline (β-isomer) hydrochloride To a 361 mg portion of the β-isomer of N-[(R)-1-ethoxycarbonyl-2-heptyldithioethyl]-alanyl-(S)-proline t-butyl ester maleate obtained in Example 5 was added a saturated aqueous solution of sodium hydrogencarbonate and the mixture was extracted with dichloromethane. The organic phase was washed with a saturated aqueous solution of sodium chloride and dried over anhydrous sodium sulfate. The solvent was evaporated off under reduced pressure and 3 ml of 4N-hydrochloride-dioxane was added to the residue. The mixture was stirred at room temperature for 4 hours. The solvent was evaporated off under reduced pressure, giving the hydrochloride of the β-isomer of the title compound as a pale yellow oil. Yield 274 mg.

$[\alpha]_D^{21} = +6.23°$ (c=0.7, ethanol).

NMR (CD₃OD): δ 0.90 (3H, t, J=5.5 Hz), 1.35 (3H, t, J=7 Hz), 2.79 (2H, t, J=7 Hz), 4.31 (2H, q, J=7 Hz).

EXAMPLE 7

Preparation of N-[(R)-1-ethoxycarbonyl-2-(2-propylthioethylthio)ethyl]-alanyl-(S)-proline methyl ester (β-isomer) and maleate thereof A 1.5 g portion of β-isomer of N-[(R)-1-ethoxycarbonyl-2-(2-propylthioethylthio)ethyl]-alanine obtained in Reference Example 37 and 845 mg of hydrochloride of (S)-proline methyl ester were dissolved in 17 ml of DMF. To the solution was added with ice cooling and stirring a solution of 924 mg of DEPC (90% content) in 3 ml of DMF. A solution of 1.43 ml of triethylamine in 2 ml of DMF was added dropwise thereto. The mixture was stirred with ice cooling for 2 hours and then further stirred at room temperature for 15 hours. The reaction mixture was poured into ice water and the mixture was made weakly alkaline with a saturated aqueous solution of sodium hydrogen-carbonate. The mixture was extracted with ethyl acetate. The extract was sufficiently washed with water and dried over anhydrous sodium sulfate. The solvent was evaporated off under reduced pressure and the residue was purified by silica gel column chromatography (a 40:1 mixture of chloroform and methanol as an eluent), giving the β-isomer of the title compound as a colorless oil. Yield 1.74 g.

The compound obtained above was dissolved in 20 ml of methanol. To the solution was added 465 mg of maleic acid to obtain a uniform solution. The solvent was entirely evaporated off under reduced pressure and ether was added to the residue. The crystals thus precipitated were collected by filtration and recrystallized from ethyl acetate-ether, giving the maleate of the title compound. Yield 1.27 g.

M.p. 83°–84° C.

$[\alpha]_D^{26} = -63.8°$ (c=0.6, ethanol)

EXAMPLES 8 TO 19

The compounds as listed below in Table 10 were obtained by following the general procedure of Example 7.

TABLE 10

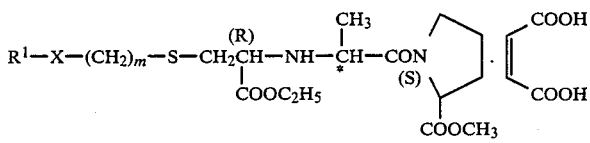

| Example No. | R¹ | X | m | Isomer (*) | Optical Rotation | M.p. (°C.) |
|---|---|---|---|---|---|---|
| 8 | $CH_3(CH_2)_2-$ | S | 3 | β | $[\alpha]_D^{25} = -59.1°$ (c=0.6, methanol) | 82–84 |
| 9 | $CH_3(CH_2)_3-$ | S | 2 | β | $[\alpha]_D^{26} = -62.5°$ (c=0.5, ethanol) | 81–82 |
| 10 | $CH_3(CH_2)_3-$ | O | 2 | β | $[\alpha]_D^{22} = -77.2°$ (c=0.5, ethanol) | 74–76 |
| 11 | $CH_3(CH_2)_5-$ | S | 2 | β | $[\alpha]_D^{25} = -52.5°$ (c=0.6, methanol) | 79–82 |
| 12 | $(CH_3)_2CH-CH_2-$ | S | 2 | β | $[\alpha]_D^{22} = -59.1°$ (c=0.7, methanol) | 95 |
| 13 | cyclohexyl | S | 2 | β | $[\alpha]_D^{25} = -56.1°$ (c=0.9, ethanol) | 83–88 |
| 14 | cyclohexyl-$CH_2-$ | S | 2 | β | $[\alpha]_D^{26} = -57.1°$ (c=0.7, ethanol) | 85–90 |
| 15 | phenyl | S | 2 | β | $[\alpha]_D^{26} = -52.8°$ (c=1.0, ethanol) | 101–102 |
| 16 | phenyl-$CH_2-$ | S | 2 | β | $[\alpha]_D^{22} = -67.2°$ (c=0.6, ethanol) | 81–84 |
| 17 | $CH_2=CH-CH_2-$ | S | 2 | α | $[\alpha]_D^{22} = +1.2°$ (c=0.7, methanol) | 74–76 |
| 18 | $(CH_3)_2C=CH-CH_2-$ | S | 2 | β | $[\alpha]_D^{23} = -57.5°$ (c=1.0, ethanol) | 62–70 |
| 19 | $H-C\equiv C-CH_2-$ | S | 2 | β | $[\alpha]_D^{22} = -76.9°$ (c=0.6, ethanol) | 99–101.5 |

EXAMPLE 20

Preparation of N-[(R)-1-ethoxycarbonyl-2-(2-phenylthioethylthio)ethyl]-alanyl-(S)-proline t-butyl ester (β-isomer)

Using 3 g of s-isomer of N-[(R)-1-ethoxycarbonyl-2-(2-phenylthioethylthio)ethyl]-alanine prepare in Reference Example 46, 1.58 of (S)-proline t-butyl ester, 1.67 g of DEPC and 1.3 ml of triethylamine and following the general procedure of Example 7, the β-isomer of the title compound was prepared as a colorless oil. Yield 3.41 g.

$[\alpha]_D^{24} = -71.7°$ (c=0.6, ethanol)

NMR (CDCl₃): δ 1.27 (3H, t, J=7 Hz), 1.28 (3H, d, J=6.5 Hz), 1.44, 1.46 (total 9H, each s), 4.18 (2H, q, J=7 Hz), 7.1–7.5 (5H, m).

EXAMPLE 21

Preparation of N-[(R)-1-ethoxycarbonyl-2-(2-phenylthioethylthio)ethyl]-alanyl-(S)-proline (β-isomer) and maleate thereof Following the general procedure of Reference Example 37, the β-isomer of the title compound was prepared as a colorless oil from 3.3 g of s-isomer of N-[(R)-1-ethoxycarbonyl-2-(2-phenylthioethylthio)ethyl]-alanyl-(S)-proline t-butyl ester obtained in Example 20.

Yield 3.0 g.

The maleate of the title compound was obtained from 3.0 g of the above compound by following the general procedure of Example 7. Yield 2.34 g.

$[\alpha]_D^{25} = -37.0°$ (c=0.7, methanol).

M.p. 83°-86° C.

EXAMPLE 22

Preparation of N-[(R)-1-carboxyl-2-(2-butoxyethylthio)ethyl]-alanyl-(S)-proline (β-isomer)

A 300 mg portion of maleate of s-isomer of N-[(R)-1-ethoxycarbonyl-2-(2-butoxyethylthio)ethyl]-alanyl-(S)-proline methyl ester prepared in Example 10 was dissolved in 1 ml of methanol. To the solution was added dropwise 3.3 ml of 1N-NaOH at room temperature. The mixture was stirred over night and neutralized with 2N-HCl with ice cooling. The solvent was completely evaporated off and the residue was dissolved in 2 ml of methanol. Insolubies were separated by filtration and the solution was subjected to high performance liquid chromatography (column: Chemcosorb 7 ODSH, 2 cm×25 cm, eluent=a 40:60:0.4 mixture of methanol, water and acetic acid, flow rate=9 ml/minute, detection=UV220 nm) for separation. The solvent was evaporated off. After addition of 2 ml of ether, the precipitated crystals were collected by filtration, giving the title compound as white crystals.

Yield 130 mg.

$[\alpha]_D^{22} = -100°$ (c=0.2, methanol).

M.p. 75°-85° C.

EXAMPLE 23

Preparation of N-[(R)-1-ethoxycarbonyl-2-[(S)-2-benzyloxycarbonylamino-3-phenylpropylthio]ethyl]-alanyl-(S)-proline methyl ester (β-isomer)

A 5 g portion of β-isomer of N-[(R)-1-ethoxycarbonyl-2-[(S)-2-benzyloxycarbonylamino-3-phenylpropylthio]ethyl]-alanine obtained in Reference Example 73 and 2.0 g of (S)-proline methyl ester hydrochloride were dissolved in 30 ml of DMF. To the solution was added with ice cooling and stirring a solution of 2.22 g of DEPC (90% content) in 10 ml of DMF. A solution of 3.2 ml of triethylamine in 10 ml of DMF was added dropwise thereto. The mixture was stirred with ice cooling for 2 hours and then further stirred at room temperature for 15 hours. The reaction mixture was poured into ice water and the mixture was made weakly alkaline with a saturated aqueous solution of sodium hydrogencarbonate, followed by extraction with ethyl acetate. The extract was sufficiently washed with water and dried over anhydrous sodium sulfate. The solvent was evaporated off under reduced pressure and the residue was purified by silica gel column chromatography (a 40:1 mixture of chloroform and methanol as an eluent), giving the title compound as a colorless oil. Yield 4.86 g.

$[\alpha]_D^{22} = -61.5°$ (c=0.8, methanol).

NMR (CDCl₃): δ 1.27 (3H, t, J=7 Hz), 1.30 (3H, d, J=7 Hz), 1.7-2.1 (4H, m), 2.6-3.1 (6H, m) 3.69, 3.72 (total 3H, each s), 4.18 (2H, q, J=7 Hz), 5.04 (2H, s), 7.23 (5H, s), 7.30 (5H, s).

EXAMPLES 24 TO 43

The compounds as listed below in Table 11 were obtained by following the general procedure of Example 23.

TABLE 11

$$R^1-X-(Y)_n-S-CH_2\overset{(R)}{\underset{COOC_2H_5}{CH}}-NH-\overset{CH_3}{\underset{*}{CH}}-CON\underset{(S)}{\diagdown}$$

$$COOR^2$$

| Example No. | $R^1$ | $-X-(Y)_n-$ | $R^2$ | Isomer (*) | Optical Rotation | NMR (CDCl₃): δ or M.p. (°C.) |
|---|---|---|---|---|---|---|
| 24 (maleate) | Z | $-NH-\underset{(R)}{\overset{CH_2-\text{Ph}}{\underset{|}{CH}}CH_2-}$ | CH₃ | α | $[\alpha]_D^{23} = -8.2°$ (c=1.0, methanol) | 89-91 |
| 25 (maleate) | Z | $-NH-\underset{(S)}{\overset{CH_2-\text{Ph}}{\underset{|}{CH}}CH_2-}$ | CH₃ | α | $[\alpha]_D^{22} = +19.2°$ (c=0.8, methanol) | 119-120 |

TABLE 11-continued $$R^1-X-(Y)_n-S-CH_2\overset{(R)}{\underset{COOC_2H_5}{CH}}-NH-\overset{CH_3}{\underset{*}{CH}}-CON\overset{(S)}{\underset{COOR^2}{\bigcirc}}$$

| Example No. | $R^1$ | $-X-(Y)_n-$ | $R^2$ | Isomer (*) | Optical Rotation | NMR (CDCl$_3$): δ or M.p. (°C.) |
|---|---|---|---|---|---|---|
| 26 | Boc | $-NH-\underset{(S)}{CH}CH_2-$ with $CH_2$-phenyl | CH$_3$ | β | $[\alpha]_D^{21} = -60.9°$ (c=0.7, ethanol) | 1.28 (3H, t, J=7Hz), 1.31 (3H, d, J=7Hz), 1.40 (9H, s), 1.8–2.3 (4H, m), 2.6–3.0 (6H, m), 3.72, 3.74 (total 3H, each s), 4.18 (2H, q, J=7Hz), 7.24 (5H, s) |
| 27 | Z | $-NH-\underset{(S)}{CH}CH_2-$ with $CH_2$-phenyl | t-Bu | β | $[\alpha]_D^{20} = -66.3°$ (c=0.4, ethanol) | 1.26 (3H, t, J=7Hz), 1.30 (3H, d, J=7Hz), 1.43 (9H, s), 1.7–2.0 (4H, m), 2.7–3.1 (6H, m), 4.18 (2H, q, J=7Hz), 5.04 (2H, s), 7.26 (5H, s), 7.30 (5H, s) |
| 28 | Z | $-NH-\underset{(R)}{CH}CH_2-$ with $CH_2$-phenyl | t-Bu | β | $[\alpha]_D^{20} = -57.2°$ (c=0.5, ethanol) | 1.26 (3H, t, J=7Hz), 1.26 (3H, d, J=7Hz), 1.7–2.3 (4H, m), 2.4–3.0 (6H, m), 4.17 (2H, q, J=7Hz), 5.07 (2H, s), 7.23 (5H, s), 7.30 (5H, s) |
| 29 | Troc | $-N\bigcirc-(CH_2)_2-$ (piperidine) | CH$_3$ | β | $[\alpha]_D^{24} = -45.1°$ (c=0.6, methanol) | 94–96 |
| 30 | Z | $-NH-\underset{(R)}{CH}CH_2-$ with phenyl | CH$_3$ | β | $[\alpha]_D^{22} = -58.2°$ (c=0.7, ethanol) | 1.25 (3H, t, J=7Hz), 1.29 (3H, d, J=7Hz), 1.9–2.2 (4H, m), 2.5–3.1 (4H, m), 3.70, 3.72 (total 3H, each s), 4.16 (2H, q, J=7Hz), 5.08 (2H, s), 7.31 (5H, s) |
| 31 | Z | $-NH-\underset{(R)}{CH}CH_2-$ with $CH_2$-phenyl | CH$_3$ | β | $[\alpha]_D^{23} = -70.7°$ (c=0.9, methanol) | 1.26 (3H, t, J=7Hz), 1.26 (3H, d, J=7Hz), 1.8–2.1 (4H, m), 2.6–3.0 (6H, m), 3.66, 3.74 (total 3H, each s), 4.18 (2H, q, J=7Hz), 5.08 (2H, s), 7.24 (5H, s), 7.31 (5H, s) |
| 32 | Z | $-NH-(CH_2)_2-$ | t-Bu | β | $[\alpha]_D^{28} = -83.6°$ (c=0.4, ethanol) | 1.27 (3H, t, J=7Hz), 1.29 (3H, d, J=7Hz), 1.42, 1.45 (total 9H, each s), 1.8–2.2 (4H, m), 3.2–3.7 (6H, m), 4.19 (2H, q, J=7Hz), 5.10 (2H, s), 7.33 (5H, s) |
| 33 | Troc | $-\underset{(CH_2)_2CH_3}{N}-(CH_2)_2-$ | CH$_3$ | β | | 0.91 (3H, t, J=7Hz), 1.32, 1.34 (total 3H, each t, J=7Hz), 3.72, 3.76 (total 3H, each s), 4.28 (2H, q, J=7Hz), 4.73 (2H, s) |

TABLE 11-continued $$R^1-X-(Y)_n-S-CH_2\overset{(R)}{\underset{COOC_2H_5}{CH}}-NH-\overset{CH_3}{\underset{*}{C}}H-CON\begin{pmatrix}(S)\\COOR^2\end{pmatrix}$$

| Example No. | $R^1$ | $-X-(Y)_n-$ | $R^2$ | Isomer (*) | Optical Rotation | NMR (CDCl$_3$): δ or M.p. (°C.) |
|---|---|---|---|---|---|---|
| 34 (benzene sulfonate) | Z | $\begin{array}{c}H_3C\quad CH_3\\\diagdown\!/\\CH\\\vert\\-NH-CHCH_2-\\(S)\end{array}$ | CH$_3$ | β | $[\alpha]_D^{22} = -31.2°$ (c=1.0, ethanol) | 0.92 (3H, d, J=6.5Hz), 0.95 (3H, d, J=6.5Hz), 1.31, 1.34 (total 3H, each t, J=7Hz), 1.58, 1.62 (total 3H, each d, J=7Hz), 1.7–2.1 (4H, m), 3.70, 3.75 (total 3H, each s), 5.10 (2H, s), 7.58 (5H, s), 7.3–7.9 (5H, m), Solvent=CD$_3$OD |
| 35 | Z | $\begin{array}{c}H_3C\quad CH_3\\\diagdown\!/\\CH\\\vert\\-NH-CHCH_2-\\(S)\end{array}$ | t-Bu | β | $[\alpha]_D^{20} = -68.0°$ (c=1.1, ethanol) | 0.92 (3H, d, J=6.5Hz), 0.95 (3H, d, 6.5Hz), 1.27 (3H, t, J=7Hz), 1.29 (3H, d, J=7Hz), 1.42, 1.45 (total 9H, each s), 1.7–2.1 (4H, m), 4.19 (2H, q, J=7Hz), 5.10 (2H, s), 7.33 (5H, s) |
| 36 | Boc | $-NH-(CH_2)_2-$ | t-Bu | β | $[\alpha]_D^{23} = -72.3°$ (c=0.5, ethanol) | 1.28 (3H, t, J=7Hz), 1.30 (3H, d, J=7Hz), 1.44, 1.46 (total 18H, each s), 1.8–2.1 (4H, m), 2.5–3.0 (4H, m), 4.20 (2H, q, J=7Hz), 4.3–4.5 (1H, m) |
| 37 | Boc | $-NH-(CH_2)_3-$ | CH$_3$ | β | $[\alpha]_D^{18} = -117.5°$ (c=0.5, ethanol) | 1.29 (3H, t, J=7Hz), 1.30 (3H, d, J=7Hz), 1.44, 1.45 (total 9H, each s), 3.71, 3.75 (total 3H, each s), 4.20 (2H, q, J=7Hz) |
| 38 | Boc | $-NH-(CH_2)_6-$ | t-Bu | β | $[\alpha]_D^{20} = -60.4°$ (c=0.7, ethanol) | 1.29 (3H, t, J=7Hz), 1.29 (3H, d, J=7Hz), 1.44, 1.47 (total 18H, each s), 4.20 (2H, q, J=7Hz), |
| 39 | Z | $\begin{array}{c}H_3C\quad CH_2CH_3\\\diagdown\!/\\(S)CH\\\vert\\-NH-CHCH_2-\\(S)\end{array}$ | CH$_3$ | β | $[\alpha]_D^{22} = -57.6°$ (c=0.7, ethanol) | 0.8–1.1 (6H, m), 1.27 (3H, t, J=7Hz), 1.29 (3H, d, J=7Hz), 2.6–3.1 (4H, m), 3.69, 3.72 (total 3H, each s), 4.19 (2H, q, J=7Hz), 5.09 (2H, s), 7.33 (5H, s) |
| 40 (maleate) | Troc |  | CH$_3$ | β | $[\alpha]_D^{23} = -80.3°$ (c=0.6, ethanol) | 124–126 |
| 41 (maleate) | Troc | 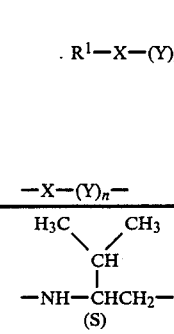 | CH$_3$ | β | $[\alpha]_D^{22} = -53.7°$ (c=0.5, ethanol) | 94–97 |
| 42 (maleate) | Troc | $-O-(CH_2)_2-$ | CH$_3$ | β | $[\alpha]_D^{23} = -57.6°$ (c=0.9, ethanol) | 110–113 |

TABLE 11-continued

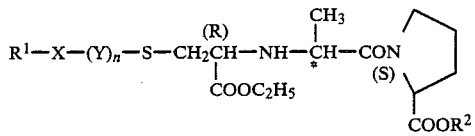

| Example No. | R¹ | —X—(Y)$_n$— | R² | Isomer (*) | Optical Rotation | NMR (CDCl$_3$): δ or M.p. (°C.) |
|---|---|---|---|---|---|---|
| 43 | PhCO | H$_3$C\\(S)CH/CH$_2$CH$_3$<br>    \|<br>—NH—CHCH$_2$—<br>    (S) | t-Bu | β | $[\alpha]_D^{23} = -35.0°$ (c=0.6, ethanol) | 0.8–1.1 (6H, m), 1.25 (3H, t, J=7Hz), 1.28 (3H, d, J=7Hz), 1.42, 1.45 (total 9H, each s), 2.7–3.1 (4H, m) 4.12, 4.16 (total 2H, each q, J=7Hz), 7.3–7.9 (5H, m) |

EXAMPLE 44

Preparation of N-[(R)-1-ethoxycarbonyl-2-(2-propylaminoethylthio)ethyl]-alanyl-(S)-proline methyl ester (β-isomer) and maleate thereof In 15 ml of acetic acid was dissolved 890 mg of β-isomer of N-[(R)-1-ethoxycarbonyl-2-[2-(N-2,2,2-trichloroethoxycarbonyl-N-propylamino)ethylthio]ethyl]-alanyl-(S)-proline methyl ester prepared in Example 33. To the solution was added 1.6 g of zinc powder and the mixture was stirred at room temperature for 4 hours. The zinc powder was filtered off. The filtrate was evaporated off under reduced pressure and the residue was poured into ice water and the mixture was adjusted to a pH of 8 to 9 with a saturated aqueous solution of sodium hydrogencarbonate. The mixture was extracted with ethyl acetate. The extract was washed with a saturated aqueous solution of sodium chloride and dried over anhydrous sodium sulfate. The solvent was evaporated off under reduced pressure, giving the s-isomer of the title compound as a colorless oil. Yield 380 mg.

The compound obtained above (380 mg) was dissolved in 25 ml of ethyl acetate and 221 mg of maleic acid was added to the solution. The solvent was evaporated off under reduced pressure and ether was added to the residue. The crystals thus precipitated were collected by filtration and recrystallized from ethyl acetate-ether, producing the maleate of the title compound.

Yield 421 mg.
M.p. 103°–107° C.
$[\alpha]_D^{24} = -69.9°$ (c=0.5, methanol).

EXAMPLES 45 AND 46

The compounds as listed below in Table 12 were obtained by following the general procedure of Example 44.

TABLE 12

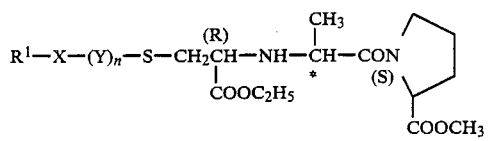

ph: phenyl group

| Example No. | R¹X—(Y)$_n$— | Isomer (*) | Optical Rotation | M.p. (°C.) |
|---|---|---|---|---|
| 45 (dimaleate) | phCH$_2$NH—(CH$_2$)$_2$— | β | $[\alpha]_D^{22} = -63.1°$ (c=0.6, ethanol) | 122–125 |
| 46 (maleate) | HO—(CH$_2$)$_2$— | β | $[\alpha]_D^{23} = -86.7°$ (c=0.8, ethanol) | 90–92 |

EXAMPLE 47

Preparation of N-[(R)-1-ethoxycarbonyl-2-[(S)-2-amino-3phenylpropylthio]ethyl]-alanyl-(S)-proline methyl ester (β-isomer) dihydrobromide In 10 ml of 25% HBr-acetic acid was dissolved 2 g of β-isomer of N-[(R)-1-ethoxycarbonyl-2-[(S)-2-benzyloxycarbonylamino-3-phenylpropylthio]ethyl]-alanyl-(S)-proline methyl ester prepared in Example 23. The solution was stirred at room temperature for 1.5 hours. The solvent was evaporated off under reduced pressure. To the residue was added ether to precipitate crystals which were collected by filtration as the title compound. Yield 2.1 g.

$[\alpha]_D^{23} = -33.9°$ (c=0.7, methanol).

NMR (CD$_3$OD): δ 1.31 (3H, t, J=7 Hz), 1.65 (3H, d, J=7 Hz), 3.70, 3.76 (total 3H, each s), 4.2–4.4 (2H, m), 4.5–4.8 (2H, m), 7.2–7.5 (5H, m).

MS: m/z=466 (M+H)+, 309, 299, 285.

EXAMPLES 48 TO 50

The compounds as listed below in Table 13 were obtained by following the general procedure of Example 47.

solution was stirred at room temperature for 2 hours. The solvent was evaporated off under reduced pressure. To the residue was added ether to precipitate crystals which were collected by filtration as the title compound.

TABLE 13

$$R^1-A-S-CH_2CH(R)-NH-\overset{*}{C}H(CH_3)-CON\underset{(S)}{\diagup}\diagdown \cdot 2HBr$$
$$\underset{COOC_2H_5}{|} \quad \quad \quad \quad COOCH_3$$

| Example No. | $R^1-A-$ | Isomer (*) | MS (m/z) | Optical Rotation | NMR (CD$_3$OD): δ |
|---|---|---|---|---|---|
| 48 | H$_3$C\\(S)CH/CH$_2$CH$_3$<br>H$_2$N—CH(S)—CH$_2$— | β | 432 (M+H)$^+$<br>299, 285,<br>275 | $[α]_D^{24} = -28.4°$<br>(c=0.8, methanol) | 0.99 (3H, t, J=7Hz),<br>1.03 (3H, d, J=7Hz),<br>1.36 (3H, t, J=7Hz),<br>1.66 (3H, d, J=7Hz),<br>3.71, 3.77 (total 3H, each s),<br>4.36 (2H, q, J=7Hz),<br>4.5–4.8 (2H, m) |
| 49 | CH$_2$ph<br>H$_2$N—CH(R)—CH$_2$— | β | 466 (M+H)$^+$<br>309, 299,<br>285 | $[α]_D^{23} = -60.2°$<br>(c=0.7, methanol) | 1.34 (3H, t, J=7Hz),<br>1.65 (3H, q, J=7Hz),<br>3.71, 3.76 (total 3H, each s),<br>4.32 (2H, q, J=7Hz),<br>4.5–4.8 (2H, m),<br>7.2–7.5 (5H, m) |
| 50 | H$_3$C\\(S)CH/CH$_2$CH$_3$<br>H$_2$N—CH(S)—CH$_2$— | α | 432 (M+H)$^+$<br>299, 285,<br>275 | $[α]_D^{24} = +31.2°$<br>(c=0.7, methanol) | 0.98 (3H, t, J=7Hz),<br>1.03 (3H, d, J=7Hz),<br>1.37 (3H, d, J=7Hz),<br>1.61 (3H, d, J=7Hz),<br>3.75, 3.78 (total 3H, each s),<br>4.36 (2H, q, J=7Hz),<br>4.5–4.8 (2H, m) |

EXAMPLE 51

Preparation of N-[(R)-1-ethoxycarbonyl-2-[(S)-2-amino-3methylbutyl-thio]ethyl]-alanyl-(S)-proline (β-isomer) dihydrobromide In 3 ml of 25% of HBr-acetic acid was dissolved 1.5 g of β-isomer of N-[(R)-1-ethoxycarbonyl-2-[(S)-2-benzyloxycarbonylamino-3-methylbutylthio]ethyl]-alanyl-(S)-proline t-butyl ester prepared in Example 35. The Yield 830 mg.
$[α]_D^{23} = -47.6°$ (c=1.1, ethanol)
M.p. 104°–121° C.

EXAMPLES 52 TO 61

The compounds as listed below in Table 14 were obtained by following the general procedure of Example 1.

TABLE 14

$$R^1-X-(Y)_n-S-CH_2CH(R)-NH-\overset{*}{C}H(CH_3)-CON\underset{(S)}{\diagup}\diagdown$$
$$\underset{COOC_2H_5}{|} \quad \quad \quad \quad COOR^2$$

| Example No. | $R^1-X-(Y)_n-$ | $R^2$ | Isomer (*) | Optical Rotation | NMR (CDCl$_3$): δ or M.p. (°C.) |
|---|---|---|---|---|---|
| 52 | CH$_3$(CH$_2$)$_3$O(CH$_2$)$_2$— | t-Bu | β | $[α]_D^{22} = -95.7°$<br>(c=0.5, ethanol) | 0.91 (3H, t, J=7Hz),<br>1.28 (3H, t, J=7Hz),<br>1.29 (3H, d, J=7Hz),<br>1.44, 1.46 (total 9H, each s),<br>4.19 (2H, q, J=7Hz) |
| 53 | CH$_3$(CH$_2$)$_3$S(CH$_2$)$_2$— | t-Bu | β | $[α]_D^{23} = -64.6°$<br>(c=1.8, ethanol) | 0.99 (3H, t, J=6.5Hz),<br>1.28 (3H, t, J=7Hz),<br>1.29 (3H, d, J=7Hz),<br>1.44, 1.46 (total 9H, each s),<br>4.20 (2H, q, J=7Hz) |

TABLE 14-continued $$R^1-X-(Y)_n-S-\underset{\underset{COOC_2H_5}{|}}{\overset{(R)}{C}H_2\overset{}{C}H}-NH-\underset{*}{\overset{CH_3}{\underset{(S)}{C}H}}-CON\underset{COOR^2}{\diagdown}$$

| Example No. | R¹—X—(Y)ₙ— | R² | Isomer (*) | Optical Rotation | NMR (CDCl₃): δ or M.p. (°C.) |
|---|---|---|---|---|---|
| 54 (maleate) | cyclohexyl-S(CH₂)₂— | t-Bu | β | $[\alpha]_D^{25} = -54.7°$ (c=1.0, methanol) | 72.5–74 |
| 55 (maleate) | cyclopentyl-S(CH₂)₂— | CH₃ | β | $[\alpha]_D^{24} = -57.8°$ (c=1.0, methanol) | 100–102 |
| 56 (maleate) | cyclopentyl-S(CH₂)₂— | t-Bu | β | $[\alpha]_D^{24} = -44.9°$ (c=0.7, methanol) | 94–97 |
| 57 (maleate) | cyclopentyl-O(CH₂)₂— | CH₃ | β | $[\alpha]_D^{25} = -81.0°$ (c=1.0, ethanol) | 68–71 |
| 58 (maleate) | cyclohexyl-Troc-N(CH₂)₂— | CH₃ | α | $[\alpha]_D^{25} = +0.46°$ (c=0.7, methanol) | 71–77 |
| 59 | cyclohexyl-Troc-N(CH₂)₂— | CH₃ | β | $[\alpha]_D^{25} = -55.9°$ (c=0.8, ethanol) | 1.29 (3H, t, J=7Hz), 1.30 (3H, d, J=7Hz), 1.4–2.3 (14H, m), 3.70, 3.74 (total 3H, each s), 4.20 (2H, q, J=7Hz), 4.3–4.6 (1H, m), 4.77 (2H, s) |
| 60 | cyclohexyl-Troc-N(CH₂)₂— | t-Bu | β | $[\alpha]_D^{25} = -51.3°$ (c=1.0, ethanol) | 1.28 (3H, d, J=7Hz), 1.29 (3H, t, J=7Hz), 1.44, 1.46 (total 9H, each s), 1.4–2.3 (14H, m), 4.20 (2H, q, J=7Hz), 4.3–4.5 (1H, m), 4.77 (2H, s) |
| 61 (maleate) | cyclopentyl-S(CH₂)₃— | CH₃ | β | $[\alpha]_D^{23} = -64.0°$ (c=0.8, ethanol) | 94–96 |

EXAMPLES 62 TO 65

The compounds as listed below in Table 15 were obtained by following the general procedure of Example 21.

TABLE 15

$$R^1-X-(Y)_n-S-CH_2\underset{COOC_2H_5}{\overset{(R)}{CH}}-NH-\underset{*}{\overset{CH_3}{\underset{|}{CH}}}-CON\diagdown\text{(S)}\diagdown COOH$$

| Example No. | $R^1$ | $-X-(Y)_n-$ | Isomer (*) | Optical Rotation (methanol) | M.p. (°C.) |
|---|---|---|---|---|---|
| 62 (benzene sulfonate) | $CH_3(CH_2)_3-$ | $-O(CH_2)_2-$ | β | $[\alpha]_D^{23} = -53.6°$ (c=0.6) | 55–57 |
| 63 (benzene sulfonate) | $CH_3(CH_2)_3-$ | $-S(CH_2)_2-$ | β | $[\alpha]_D^{23} = -37.0°$ (c=0.7) | 99–103 |
| 64 (L-Arg salt) | cyclohexyl | $-S(CH_2)_2-$ | β | $[\alpha]_D^{21} = -50.0°$ (c=1.0) | 63–81 |
| 65 (L-Arg salt) | cyclopentyl | $-S(CH_2)_2-$ | β | $[\alpha]_D^{25} = -52.1°$ (c=0.7) | 75–97 |

EXAMPLES 66 TO 67

The compounds as listed below in Table 16 were obtained by following the general procedure of Example 44.

TABLE 16

$$\text{cyclohexyl}-NH(CH_2)_2S-CH_2\underset{COOC_2H_5}{\overset{(S)}{CH}}-NH-\underset{*}{\overset{CH_3}{\underset{|}{CH}}}-CON\diagdown\text{(S)}\diagdown COOCH_3 \cdot .2\diagdown\overset{COOH}{\underset{COOH}{}}$$

| Example No. | Optical Rotation (methanol) | M.p. (°C.) | Isomer (*) |
|---|---|---|---|
| 66 | $[\alpha]_D^{25} = -16.0°$ (c=0.7) | 111–118 | α |
| 67 | $[\alpha]_D^{25} = -58.2°$ (c=1.0) | 112–115.5 | β |

Given below are preparation examples illustrating the preparation of pharmaceutical compositions containing the compounds of the invention.

Preparation Example 1

Preparation of tablets

One thousand tablets for oral administration each containing 5 mg of maleate of N-[(R)-1-ethoxycarbonyl-2(2-cyclopentylthioethylthio)ethyl]-alanyl-(S)-proline methyl ester (β-isomer) were prepared according to the following formulation.

| Component | Amount (g) |
|---|---|
| Maleate of N-[(R)-1-ethoxycarbonyl-2-(2-cyclopentylthioethylthio)ethyl]-alanyl-(S)-proline methyl ester (β-isomer) | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

The maleate of N-[(R)-1-ethoxycarbonyl-2-(2-cyclopentylthioethylthio)ethyl]-alanyl-(S)-proline methyl ester (β-isomer), lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

Preparation Example 2

Preparation of capsules

One thousand hard gelatin capsules for oral administration each containing 10 mg of maleate of N-[(R)-1-ethoxycarbonyl-2-(2-cyclopentylthioethylthio)ethyl]-alanyl-(S)-proline methyl ester (β-isomer) were prepared according to the following formulation.

| Component | Amount (g) |
|---|---|
| Maleate of N-[(R)-1-ethoxycarbonyl-2-(2-cyclopentylthioethylthio)ethyl]-alanyl-(S)-proline methyl ester (β-isomer) | 10 |
| Lactose (according to Japanese Pharmacopoeia) | 80 |
| Starch (according to Japanese | 30 |

| Component | Amount (g) |
| --- | --- |
| Pharmacopoeia) | |
| Talc (according to Japanese Pharmacopoeia) | 5 |
| Magnesium stearate (according to Japanese Pharmacopoeia) | 1 |

The foregoing components were finely divided and thoroughly stirred to obtain a homogeneous mixture. The mixture was enclosed in capsules for oral administration having the desired size.

Preparation Example 3

Preparation of injections

A sterilized aqueous solution for parenteral administration was prepared according to the following formulation.

| Component | Amount (g) |
| --- | --- |
| N-[(R)-1-ethoxycarbonyl-2-(2-cyclopentylthioethylthio)ethyl]-alanyl-(S)-proline methyl ester ($\beta$-isomer) maleate | 1 |
| Polyethylene glycol having a molecular weight of 4,000 (according to Japanese Pharmacopoeia) | 0.3 |
| Sodium chloride (according to Japanese Pharmacopoeia) | 0.9 |
| Polyoxyethylene sorbitan monooleate (according to Japanese Pharmacopoeia) | 0.4 |
| Sodium metabisulfite (according to Japanese Pharmacopoeia) | 0.1 |
| Methylparaben (according to Japanese Pharmacopoeia) | 0.18 |
| Propylparaben (according to Japanese Pharmacopoeia) | 0.02 |
| Distilled water for injection | 100 (ml) |

The foregoing parabens, sodium metabisulfite and sodium chlorite were dissolved at 80° C. in about 50 ml of distilled water for injection while being stirred. The solution was cooled to 40° C. In the solution were dissolved N-[(R)-1-ethoxycarbonyl-2(2-cyclopentylthioethylthio)ethyl]-alanyl-(S)-proline methyl ester ($\beta$-isomer) maleate, polyethylene glycol and polyoxyethylene sorbitan monooleate. Distilled water for injection (about 50 ml) was added to the solution to adjust the final regulated volume, and the mixture was sterilized by sterile filtration using suitable filter paper. One milliliter of the solution was introduced into separate ampoules to make injectables.

Preparation Example 4

Preparation of tablets

One thousand tablets for oral administration each containing 5 mg of maleate of N-[(R)-1-ethoxy-carbonyl-2-(2-butoxyethylthio)ethyl]-alanyl-(S)-proline methyl ester ($\beta$-isomer) were prepared according to the following formulation.

| Component | Amount (g) |
| --- | --- |
| N-[(R)-1-ethoxycarbonyl-2-(2-butoxyethylthio)ethyl]-alanyl-(S)-proline methyl ester ($\beta$-isomer) maleate | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

N-[(R)-1-ethoxycarbonyl-2-(2-butoxyethylthio)ethyl]-alanyl-(S)-proline methyl ester ($\beta$-isomer) maleate, lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

Preparation Example 5

Preparation of tablets

One thousand tablets for oral administration each containing 5 mg of N-[(R)-1-ethoxycarbonyl-2-(2-butoxyethylthio)ethyl]-alanyl-(S)-proline ($\beta$-isomer) maleate were prepared according to the following formulation.

| Component | Amount (g) |
| --- | --- |
| Maleate of N-[(R)-1-ethoxycarbonyl-2-(2-butoxyethylthio)ethyl]-alanyl-(S)-proline ($\beta$-isomer) | 5 |
| Lactose (according to Japanese Pharmacopoeia) | 50 |
| Corn starch (according to Japanese Pharmacopoeia) | 25 |
| Crystalline cellulose (according to Japanese Pharmacopoeia) | 25 |
| Methyl cellulose (according to Japanese Pharmacopoeia) | 1.5 |
| Magnesium stearate (according to Japanese Pharmacopoeia) | 1 |

N-[(R)-1-ethoxycarbonyl-2-(2-butoxyethylthio)ethyl]-alanyl-(S)-proline ($\beta$-isomer) maleate, lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

Preparation Example 6

Preparation of tablets

One thousand tablets for oral administration each containing 5 mg of maleate of N-[(R)-1-ethoxy-carbonyl-2-(2-cyclohexylthioethylthio)ethyl]-alanyl-(S)-proline methyl ester ($\beta$-isomer) were prepared according to the following formulation.

| Component | Amount (g) |
| --- | --- |
| N-[(R)-1-ethoxycarbonyl-2-(2-cyclohexylthioethylthio)ethyl]-alanyl-(S)-proline methyl ester ($\beta$-isomer) maleate | 5 |
| Lactose (according to Japanese Pharmacopoeia) | 50 |
| Corn starch (according to Japanese Pharmacopoeia) | 25 |
| Crystalline cellulose (according to Japanese Pharmacopoeia | 25 |
| Methyl cellulose (according to Japanese | 1.5 |

| Component | Amount (g) |
|---|---|
| Pharmacopoeia) | |
| Magnesium stearate (according to Japanese Pharmacopoeia) | 1 |

The maleate of N-[(R)-1-ethoxycarbonyl-2-(2-cyclohexylthioethylthio)ethyl]-alanyl-(S)-proline methyl ester (62 -isomer), lactose, corn starch and crystalline cellulose were thoroughly mixed together and granulated with a 5% aqueous solution of methyl cellulose. The granules thus obtained were passed through a 200-mesh sieve and mixed with magnesium stearate and the mixture was pressed into tablets.

Pharmacological Test 1

Inhibitory activity against angiotensin-converting enzyme (ACE)

A 10 μM quantity of the compound of the present invention was dissolved in 50 ml of a phosphate buffer (pH 8.3). The solution was diluted with the same phosphate buffer as above to prepare a sample solution.

A 100 μl quantity of an enzyme solution prepared from rat lung was mixed with 100 μl of the sample solution. The mixture was gently shaken at 37° C. for 10 minutes. To the mixture was added 100 μl of a solution containing 6.99 mM of hippuryl-histidyl-leucine (product of Peptide Institute, Inc., Japan) as a substrate. The resulting mixture was incubated at 37° C. for 10 minutes. The reaction was terminated by addition of 100 μl of a 10% metaphosphoric acid to the reaction mixture and the mixture was neutralized with 1N-sodium hydroxide. A 10 μl quantity of the resulting mixture was subjected to high performance liquid chromatography (HPLC) for analysis. The area valve (S) of the hippuric acid formed by the reaction was measured. A control area valve (R) was measured by repeating the same procedure as above except that 100 μl of phosphate buffer (pH 8.3) was used in place of the sample solution.

A percent inhibition was calculated by the following equation:

$$\text{Percent Inhibition (\%)} = \frac{R - S}{R} \times 100$$

The inhibitory activity was expressed as $IC_{50}$, i.e., the concentration of the sample solution in the reaction mixture in which concentration 50% inhibition is achieved.

Table 17 below shows the result of the test conducted using the compounds of the invention as samples. The samples were all used in the form of dicarboxylic acid which were prepared by the same reaction as the hydrolysis described in Example 22.

TABLE 17

| Test Compound | ACE Inhibitory Activity $IC_{50}$ (mol/l) |
|---|---|
| Example 22 | $1.14 \times 10^{-10}$ |
| Example 3 | $2.54 \times 10^{-10}$ |
| Example 9 | $1.26 \times 10^{-10}$ |
| Example 45 | $7.55 \times 10^{-10}$ |
| Example 46 | $3.53 \times 10^{-9}$ |
| Example 49 | $2.71 \times 10^{-9}$ |

TABLE 17-continued

| Test Compound | ACE Inhibitory Activity $IC_{50}$ (mol/l) |
|---|---|
| Example 55 | $1.08 \times 10^{-10}$ |

We claim:

1. A proline derivative represented by the formula $$R^1-S-Y-SCH_2CH(COOR^2)-NH-CH(R^3)-CO-N\underset{COOR^4}{\underbrace{\phantom{XXX}}}$$

wherein
$R^1$ is $C_1$–$C_8$ alkyl, $C_3$–$C_8$ cycloalkyl or $C_3$–$C_8$ cycloalkyl-$C_1$–$C_6$ alkyl;
$R^2$ and $R^4$ are the same or different and each represents hydrogen or $C_1$–$C_6$ alkyl; $R^3$ is $C_1$–$C_6$ alkyl; and
Y is $C_2$ alkylene;
or a pharmaceutically acceptable salt thereof.

2. A proline derivative as defined in claim 1 wherein $R^1$ is $C_1$–$C_8$ alkyl.

3. A proline derivative as defined in claim 1 wherein $R^1$ is $C_3$–$C_8$ cycloalkyl.

4. A proline derivative as defined in claim 1 wherein $R^1$ is $C_4$–$C_6$ cycloalkyl $R^3$ is methyl.

5. A proline derivative as defined in claim 1 which is selected from the group consisting of:
N-[(R)-1-ethoxycarbonyl-2-(2-butylthioethylthio)ethyl]-alanyl-(S)-proline methyl ester (β-isomer),
N-[(R)-1-ethoxycarbonyl-2-(2-cyclohexylthioethylthio)ethyl]-alanyl-(S)-proline methyl ester (β-isomer),
N-[(R)-1-ethoxycarbonyl-2-(2-cyclopentylthioethylthio)ethyl]-alanyl-(S)-proline methyl ester (β-isomer),
N-[(R)-1-ethoxycarbonyl-2-(2-butylthioethylthio)ethyl]-alanyl-(S)-proline (β-isomer),
N-[(R)-1-ethoxycarbonyl-2-(2-cyclohexylthio)ethylthio)ethyl]-alanyl-(S)proline (β-isomer),
N-[(R)-1-ethoxycarbonyl-2-(2-cyclopentylthioethylthio)ethyl]-alanyl-(S)-proline (β-isomer), and
N-[(R)-1-ethoxycarbonyl-2-pentyldithioethyl]-alanyl-(S)-proline methyl ester (β-isomer).

6. A proline derivative as defined in claim 5 which is N-[(R)-1-ethoxycarbonyl-2-(2-cyclopentyl-thioethylthio)ethyl]-alanyl-(S)-proline (β-isomer).

7. A pharmaceutical composition for inhibiting angiotensin converting enzyme comprising an effective amount of at least one of the proline derivative and pharmaceutically acceptable salt thereof as defined in claim 1 in combination with a pharmaceutically acceptable carrier.

8. A pharmaceutical composition as defined in claim 7 wherein $R^1$ is $C_3$–$C_8$ cycloalkyl $R^3$ is $C_1$–$C_6$ alkyl, and n is 1.

9. A pharmaceutical composition as defined in claim 7 wherein $R^1$ is $C_4$–$C_6$ cycloalkyl $R^3$ is methyl.

10. A pharmaceutical composition as defined in claim 7 which is N-[(R)-1-ethoxycarbonyl-2-(2-cyclopentyl-thioethylthio)ethyl]-alanyl-(S)-proline (β-isomer).

11. A method for inhibiting angiotensin converting enzyme comprising administering to a patient of an effective amount of at least one of the proline derivative and pharmaceutically acceptable salt thereof as defined in claim 1 in an amount effective for inhibiting the angiotensin converting enzyme.

12. A method as defined in claim 11 wherein $R^1$ is $C_3$–$C_8$ cycloalkyl.

13. A method as defined in claim 11 wherein $R^1$ is $C_4$–$C_6$ cycloalkyl and $R^3$ is methyl.

14. A method as defined in claim 11 which is N-[(R)-1-ethoxycarbonyl-2-(2-cyclopentyl-thioethylthio)ethyl]-alanyl-(S)-proline ($\beta$-isomer).

* * * * *